US012607626B2

(12) United States Patent
Lind et al.

(10) Patent No.: US 12,607,626 B2
(45) Date of Patent: Apr. 21, 2026

(54) METHOD FOR SEPARATING BIOMOLECULES

(71) Applicant: Cytiva Sweden AB, Uppsala (SE)

(72) Inventors: Ola Lind, Uppsala (SE); Nils Norrman, Uppsala (SE); Sara Häggblad Sahlberg, Uppsala (SE); Ronnie Palmgren, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 1061 days.

(21) Appl. No.: 17/437,118

(22) PCT Filed: Mar. 23, 2020

(86) PCT No.: PCT/EP2020/058020
    § 371 (c)(1),
    (2) Date: Sep. 8, 2021

(87) PCT Pub. No.: WO2020/193483
    PCT Pub. Date: Oct. 1, 2020

(65) Prior Publication Data
    US 2022/0229052 A1     Jul. 21, 2022

(30) Foreign Application Priority Data

Mar. 27, 2019     (GB) ..................................... 1904225
    Oct. 1, 2019     (GB) ..................................... 1914134

(51) Int. Cl.
    *G01N 33/543*     (2006.01)
    *G01N 30/92*     (2006.01)
(52) U.S. Cl.
    CPC ....... *G01N 33/54326* (2013.01); *G01N 30/92* (2013.01)
(58) Field of Classification Search
    None
    See application file for complete search history.

(56) References Cited

U.S. PATENT DOCUMENTS 7,506,765 B2     3/2009     Franzreb et al.

FOREIGN PATENT DOCUMENTS

| CN | 101490248 A | 7/2009 | |
| CN | 105792926 A | 7/2016 | |
| JP | 2002528737 A | 9/2002 | |
| JP | 2004309189 A | * 11/2004 | |
| JP | 2008518885 A | 6/2008 | |
| WO | 2000025884 A1 | 5/2000 | |
| WO | 2006/043896 A1 | 4/2006 | |
| WO | 2008/007270 A2 | 1/2008 | |
| WO | WO-2012027747 A2 | * 3/2012 | ............ C12M 41/36 |
| WO | WO-2014031480 A1 | * 2/2014 | .............. C12N 7/00 |
| WO | 2016/034564 A1 | 3/2016 | |
| WO | 2018/122089 A1 | 7/2018 | |
| WO | 2018122246 A1 | 7/2018 | |

OTHER PUBLICATIONS

Andritz, "Separation single-stage protein purification rotor stator high-gradient magnetic separator MES-RS" (retrieved online https://www.andritz.com/resource/blob/269472/db33e03298223693667155ba878bbd1d/rotor-stator-high-gradient-magnetic-separator-mes-rs-data.pdf on Jul. 22, 2025) (Year: 2025).*
SG Office Action and Search Report with Written Opinion for SG Application No. 11202108951T, mailed Jul. 4, 2023 (12 pages).
PCT International Search Report and Written Opinion for PCT/EP2020/058020 mailed Aug. 11, 2020 (14 pages).
Great Britain Search Report for GB Application No. 1904225.8 mailed Oct. 1, 2019 (8 pages).
Ebeler et al., "One-Step Integrated Clarification and Purification of a Monoclonal Antibody using Protein A Mag Sepharose Beads and a cGMP-Compliant High-Gradient Magnetic Separator," New Biotechnology, 2018, 42:48-55.
Franzreb et al., "Protein Purification Using Magnetic Adsorbent Particles," Appl Microbiol Biotechnol, 2006, 70:505-516.
Bosnes, M. et al., "Magnetic Separation in Molecular Biology," Scientific and Clinical Applications of Magnetic Carriers, 1997: pp. 269-285.
Pershina, A.G. et al., "Application of magnetic nanoparticles in biomedicine", Bulletin of Siberian Medicine, 2008, 7(2): pp. 70-78.
Rapoport, E.M. et al., "Probing Cell Surface Lectins with Neoglycoconjugates", Analytical Technologies, 2007: pp. 397-415.
Russian Office Action and Search Reports for RU Application No. 9-P20670RU mailed Aug. 2, 2023 (19 pages with English translation).
Japanese Office Action JP Application No. 2021-557164, mailed Mar. 4, 2024 (7 pages, with English translation).
Chinese Office Action in corresponding CN Application No. 202080023921.3, mailed Aug. 31, 2024 (20 pages, with English translation).
Xiaodong Tong, et al., "Magnetically Stabilized Fluidized Bed
(Continued)

*Primary Examiner* — Christopher L Chin
*Assistant Examiner* — Fernando Ivich
(74) *Attorney, Agent, or Firm* — Eversheds-Sutherland (US) LLP

(57) ABSTRACT

The present disclosure is directed to a method for separating a biomolecule from a cell culture or from a biological solution, comprising the steps of: (a) providing magnetic particles comprising ligands capable of binding the biomolecule; (b) contacting a cell culture or a biological solution comprising the biomolecule with the magnetic particles to obtain magnetic particles comprising the bound biomolecule; (c) retaining the magnetic particles with a magnetic field in a magnetic separator; (d) optionally washing the magnetic particles with a washing liquid; (e1) providing a flow of an elution liquid through the magnetic separator to elute the bound biomolecule from the magnetic particles while retaining the magnetic particles with the magnetic field in the magnetic separator; (f1) forwarding the biomolecule eluted from the magnetic separator to a membrane chromatography device; (g1) separating the biomolecule from impurities and/or contaminants by membrane chromatography.

23 Claims, 10 Drawing Sheets

(56) References Cited

OTHER PUBLICATIONS

MSFB) for bioseparations", Chemical Industry and Engineering Progress, pp. 12, 43-45, 59, Dec. 31, 2001.

Xiuju LV, et al., "Application of magnetic field fluidized bed in biochemical engineering", Chemical Industry and Engineering Progress, 03, Whole Article, Mar. 30, 2001.

JP Office Action in corresponding Japanese Application No. 2024-152524, dated Sep. 9, 2025, 8 pages.

* cited by examiner a — Providing magnetic particles b — Contacting cell culture comprising biomolecule with magnetic particles c — Retaining magnetic particles in magnetic separator d — Washing (optional)

e — Agitating magnetic particles f — Flow elute biomolecule while retaining magnetic particles in magnetic separator

METHOD FOR SEPARATING BIOMOLECULES

CROSS REFERENCE TO RELATED APPLICATIONS

This application claims the priority benefit of PCT/EP2020/058020, filed on Mar. 23, 2020, which claims the benefit of Great Britain Application Nos. 1904225.8 and 1914134.0, filed on Mar. 27, and Oct. 1, 2019, respectively, the entire contents of which are incorporated by reference herein.

FIELD OF THE DISCLOSURE

The present disclosure relates to the field of separation of biomolecules, and in particular is directed to a method for separating biomolecules from a cell culture or from a biological solution in a magnetic separator.

BACKGROUND OF THE DISCLOSURE

Separation of biomolecules by use of magnetic adsorbent beads is known in the art. For example, U.S. Pat. No. 7,506,765 B2 describes a high-gradient magnetic separator for the selective separation of magnetic particles from a suspension which is conducted through a matrix of plate-like separation structures of a magnetic material which are disposed in a magnetic field. Further, U.S. Pat. No. 6,602, 422 B1, which is hereby incorporated by reference in its entirety, relates to a separation and release process for purifying biological material on a micro separation column. The method includes release of the biological material from magnetic carriers and elution from the micro separation column while the magnetic carriers are still magnetically retained by a matrix of ferromagnetic particles inside the micro separation column. The patent publication WO2018122246 describes a method for separating biomolecules from a cell culture, comprising binding the biomolecules to magnetic beads, separating the magnetic beads including bound biomolecules from the rest of the cell culture by use of a magnetic separator, forwarding the magnetic beads including bound biomolecules as a slurry with an added buffer to a separate elution cell, and eluting the biomolecules from the magnetic beads in the elution cell. Also, the patent publication WO2018122089 relates to magnetic beads comprising a porous matrix and one or more magnetic particles embedded in the matrix, and further comprising immunoglobulin-binding ligands covalently coupled to the porous matrix.

Magnetic bead processing is an effective way to purify a target biomolecule directly from crude feed cell stocks and this technology can replace clarification tools such as centrifugation, filtration and capture chromatography. The magnetic beads are functionalized with ligands which have affinity for the target biomolecule. The magnetic beads are added and mixed with the crude feed for a certain time to specifically bind all target biomolecules in the feed. After binding, the magnetic beads are trapped by a magnet while cells and impurities are decanted off. Wash buffer is added to the magnetic beads and the magnet is turned off and mixing is made with wash buffer and the magnetic beads. After mixing, the magnet is turned on to trap the beads and the wash buffer is decanted off. After several washings, elution buffer is added to the magnetic beads, in the same way as for the wash buffer, and the target biomolecule is released from the magnetic beads using several batch elution steps. All washing steps and elution steps are made in batch mode and since it is required to perform several batch elution steps to obtain high elution yield, the target will be more diluted using this technique compared to column chromatography. It is also, using batch elution, more difficult to optimize elution conditions since the elution buffer needs to titrate the washing buffer to reach the correct elution conditions to release the target biomolecule from the magnetic beads and that requires different or large volumes of elution buffer for each elution step. One way to overcome this is to transfer the washed beads into a chromatography column for the elution step to decrease the volume elution buffer and collect the elution pool using fractionation with one elution buffer that is optimized. However, this needs additional equipment and column packing, which is time consuming.

Thus, there is a need in the art for improved methods for separation of biomolecules, comprising efficient capture and purification of biomolecules from crude feeds, while achieving a reduced process time and a more cost-efficient process.

SUMMARY OF THE DISCLOSURE

The above objective to provide improved methods for separation of biomolecules is achieved by the present disclosure, which relates to a method for separation of biomolecules by simultaneously applying flow elution and agitation in a magnetic separator. As shown herein, it is thereby possible to flow-elute the target biomolecule directly from the magnetic separator with a surprisingly high yield and purity by use of a small elution volume. The precision of the method equals the precision of column chromatography while requiring a substantially shorter process time.

More particularly, the present disclosure is directed to a method for separating a biomolecule from a cell culture or from a biological solution, comprising the steps of:
- (a) providing magnetic particles comprising ligands capable of binding the biomolecule;
- (b) contacting a cell culture or a biological solution comprising the biomolecule with the magnetic particles to obtain magnetic particles comprising the bound biomolecule;
- (c) retaining the magnetic particles with a magnetic field in a magnetic separator;
- (d) optionally washing the magnetic particles with a washing liquid;
- (e) agitating the magnetic particles in at least one plane of the magnetic separator to form a fluidised bed of magnetic particles in the magnetic separator;
- (f) providing a flow of an elution liquid in a direction essentially perpendicular to the at least one plane, to elute the bound biomolecule from the magnetic particles while retaining the magnetic particles with the magnetic field in the magnetic separator.

A further improvement realised by the present inventors is that the magnetic separation may be followed by membrane chromatography to purify the biomolecule further. Accordingly, the present disclosure provides a method for separating a biomolecule from a cell culture or from a biological solution, comprising the steps of:
- (a) providing magnetic particles comprising ligands capable of binding the biomolecule;
- (b) contacting a cell culture or a biological solution comprising the biomolecule with the magnetic particles to obtain magnetic particles comprising the bound biomolecule;

(c) retaining the magnetic particles with a magnetic field in a magnetic separator;

(d) optionally washing the magnetic particles with a washing liquid;

(e1) providing a flow of an elution liquid through the magnetic separator to elute the bound biomolecule from the magnetic particles while retaining the magnetic particles with the magnetic field in the magnetic separator;

(f1) forwarding the biomolecule eluted from the magnetic separator to a membrane chromatography device;

(g1) separating the biomolecule from impurities and/or contaminants by membrane chromatography.

Preferred aspects of the present disclosure are described below in the detailed description and in the dependent claims.

DETAILED DESCRIPTION OF THE DISCLOSURE

Figure 1:
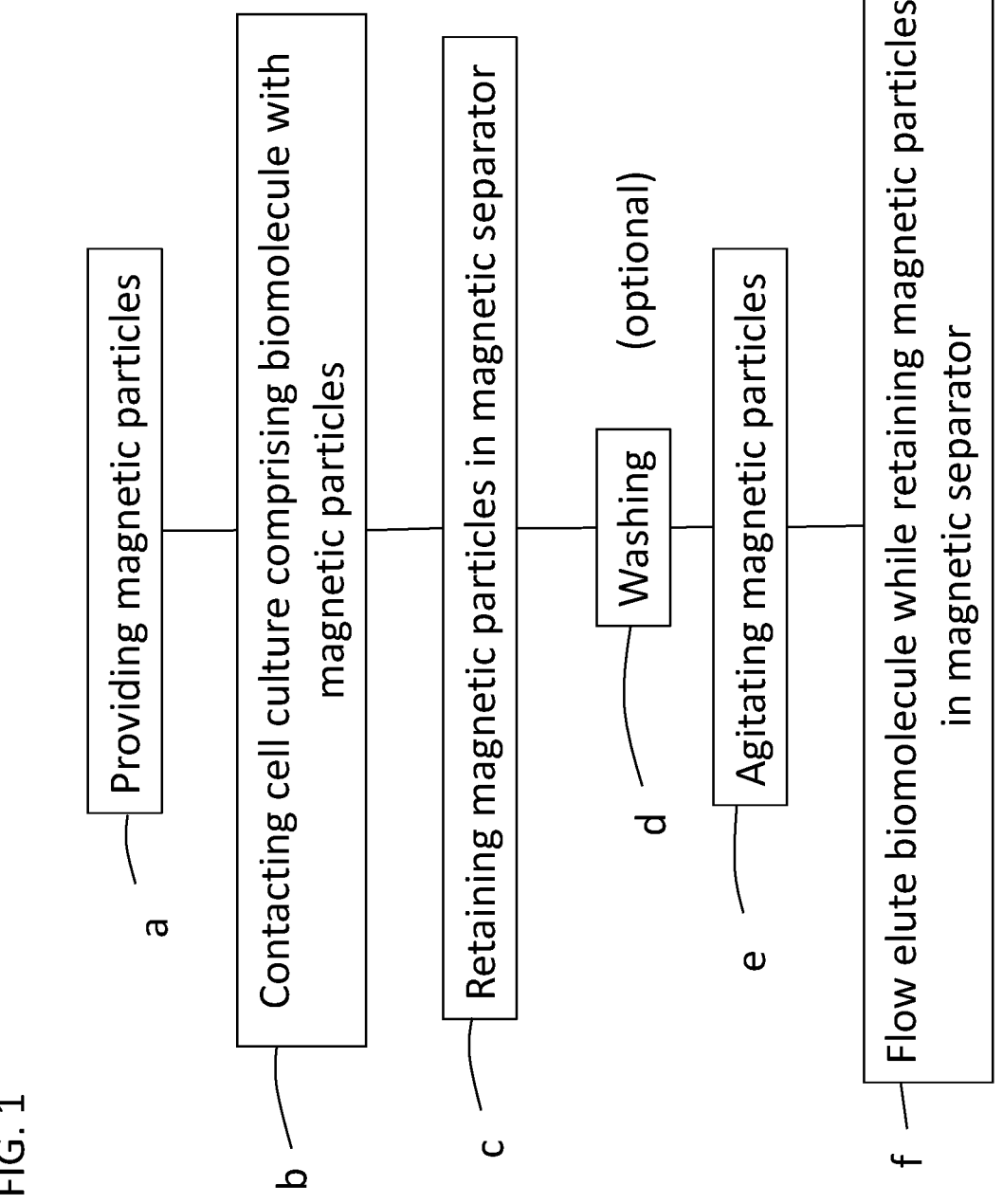
FIG. 1 is a flow chart of a method for separating a biomolecule according to the present disclosure.

The present disclosure solves or at least mitigates the problems associated with existing methods for separating biomolecules by providing, as illustrated in FIG. 1, a method for separating a biomolecule from a cell culture or from a biological solution, comprising the steps of:

(a) providing magnetic particles comprising ligands capable of binding the biomolecule;

(b) contacting a cell culture or a biological solution comprising the biomolecule with the magnetic particles to obtain magnetic particles comprising the bound biomolecule;

(c) retaining the magnetic particles with a magnetic field in a magnetic separator;

(d) optionally washing the magnetic particles with a washing liquid;

(e) agitating the magnetic particles in at least one plane of the magnetic separator to form a fluidised bed of magnetic particles in the magnetic separator;

(f) providing a flow of an elution liquid in a direction essentially perpendicular to the at least one plane, to elute the bound biomolecule from the magnetic particles while retaining the magnetic particles with the magnetic field in the magnetic separator.

A significant advantage of the presently disclosed method is that the biomolecule is eluted with a surprisingly low total elution volume, more particularly an elution volume which is a maximum of 10 bed volumes of elution liquid, such as 9, 8, 7, 6, 5, 4, 3, 2 or 1 bed volumes; preferably a maximum of 4 bed volumes, more preferably a maximum of 3 bed volumes. Herein, a "bed volume" is to be understood as the volume of sedimented magnetic particles, normally expressed in millilitres (ml or mL) or in litres (L). The lower the total elution volume required to elute a biomolecule, the more concentrated and less dispersed is the sample of eluted biomolecule. A high concentration of biomolecule is desirable in any subsequent polishing steps, in order to avoid handling large volumes of sample.

Figure 6:
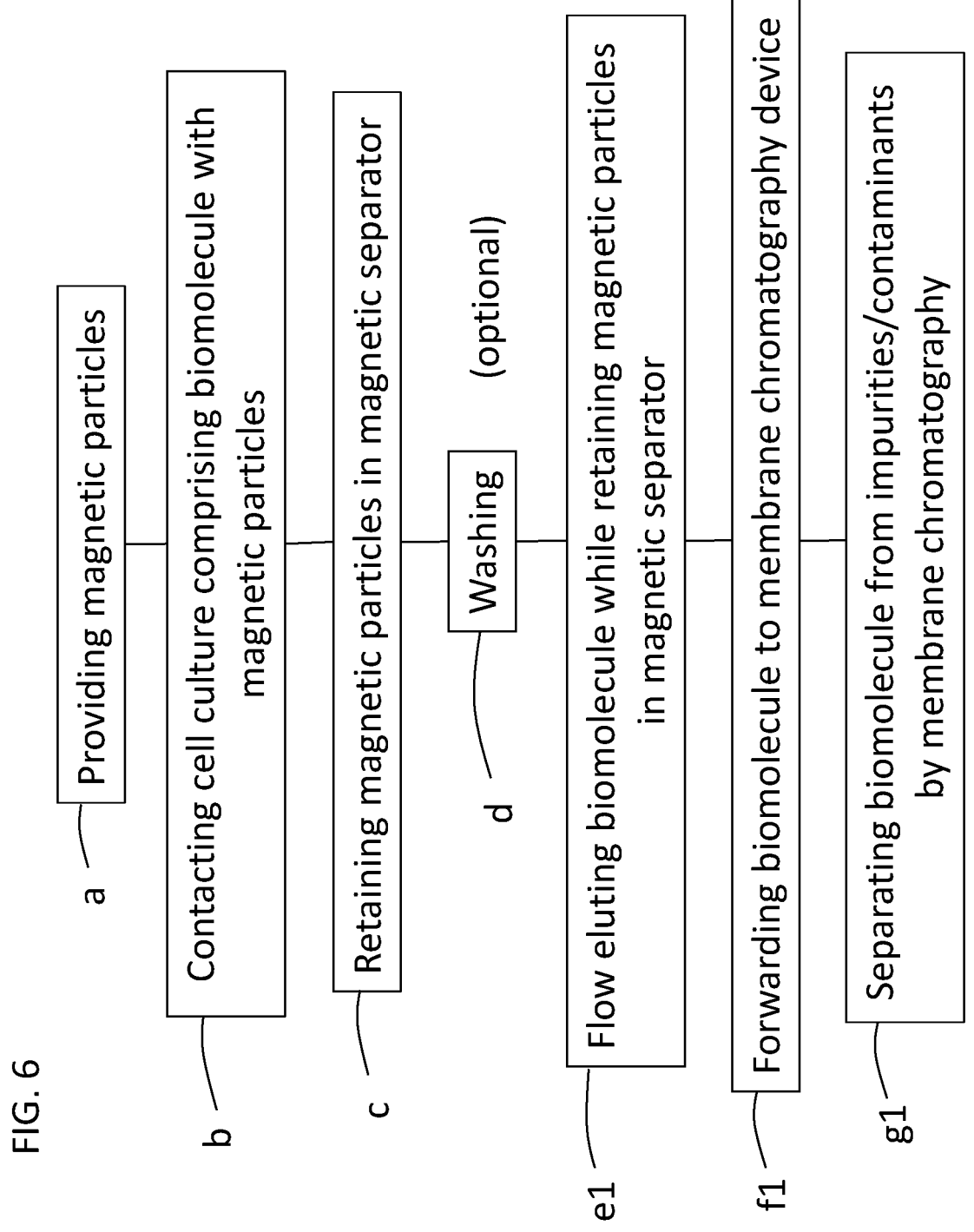
FIG. 6 is a flow chart of an alternative method for separating a biomolecule according to the present disclosure.

As mentioned above, a further improvement of the presently disclosed method may involve additional purification of the biomolecule by membrane chromatography after the magnetic separation. Thus, the present disclosure provides, as illustrated in FIG. 6, a method for separating a biomolecule from a cell culture or a biological solution, comprising the steps of:

(a) providing magnetic particles comprising ligands capable of binding the biomolecule;

(b) contacting a cell culture or a biological solution comprising the biomolecule with the magnetic particles to obtain magnetic particles comprising the bound biomolecule;

(c) retaining the magnetic particles with a magnetic field in a magnetic separator;

(d) optionally washing the magnetic particles with a washing liquid;

(e1) providing a flow of an elution liquid through the magnetic separator to elute the bound biomolecule from the magnetic particles while retaining the magnetic particles with the magnetic field in the magnetic separator;

(f1) forwarding the biomolecule eluted from the magnetic separator to a membrane chromatography device;

(g1) separating the biomolecule from impurities and/or contaminants by membrane chromatography.

The addition of membrane chromatography after the magnetic separation results in a strikingly simple and fast process which results in a high purity of the biomolecule.

The term "biomolecule" has its conventional meaning in the field of bioprocessing, in which biomolecules are produced (often recombinantly) by cells in a cell culture and purified from the cell culture by any means of separation and purification. Alternatively, the biomolecules are present in a biological solution which does not necessarily originate from a cell culture. Non-limiting examples of biomolecules are biomacromolecules, which are large biological polymers that are made up of monomers linked together, e.g. peptides and proteins (which can be native or recombinant), including but not limited to enzymes, antibodies and antibody fragments, as well as carbohydrates, and nucleic acid sequences, such as DNA and RNA. Other non-limiting examples of biomolecules are plasmids and viruses. A biomolecule or a biomacromolecule may for example be a biopharmaceutical, i.e. a biological molecule, including but not limited to a biological macromolecule, which is intended for use as a pharmaceutical compound. Herein, a biomolecule to be separated from the rest of a cell culture or a biological solution by the presently disclosed method may alternatively be referred to as a "target biomolecule" or "target". It is to be understood that "a biomolecule" is intended to mean a type of biomolecule and that the singular form of the term may encompass a large number of individual biomolecules.

Herein, the term "cell culture" refers to a culture of cells or a group of cells being cultivated, wherein the cells may be any type of cells, such as bacterial cells, viral cells, fungal cells, insect cells, or mammalian cells. A cell culture may be unclarified, i.e. comprising cells, or may be cell-depleted, i.e. a culture comprising no or few cells but comprising biomolecules released from the cells before removing the cells. Further, an unclarified cell culture as used in the presently disclosed method may comprise intact cells, disrupted cells, a cell homogenate, and/or a cell lysate.

The term "biological solution" is intended to mean a solution of biological origin, comprising a biomolecule or a mixture of several types of biomolecules. Examples of biological solutions are any type of bodily fluid originating from a human or an animal, such as plasma, blood, sputum, urine, and milk.

The term "magnetic particle" is defined herein as a particle which is able to be attracted by a magnetic field. At the same time, magnetic particles for use in the presently disclosed method shall not aggregate in the absence of a magnetic field. In other words, the magnetic particles shall behave like superparamagnetic particles. The particle may have any symmetric shape, such as a sphere or a cube, or any asymmetric shape. Spherical magnetic particles are often called magnetic beads. It is to be understood that the terms "magnetic particle", "magnetic bead", "Mag particle", "Mag bead", "magparticle" and "magbead" may be used interchangeably herein, without limiting the scope to magnetic particles having a spherical shape.

Magnetic particles suitable for use in the presently disclosed method have been described in WO2018122089, which is hereby incorporated by reference in its entirety. In particular, magnetic particles may have a volume-weighted median diameter (d50, v) in a range of from 8 to 300 μm, such as 8, 9, 10, 15, 20, 25, 30, 35, 36, 37, 38, 39, 40, 50, 60, 70, 80, 90, 95, 100, 105, 110 150, 200 250, or 300 μm, preferably in a range of from 20 to 200 μm, more preferably in a range of from 37 to 100 20 μm. Further, magnetic particles suitable for use in the presently disclosed method may have an average density of 1.05-1.20 g/ml sedimented magnetic particles.

A magnetic particle suitable for use in the presently disclosed method may comprise a porous matrix, preferably a porous polymer matrix, and one or more magnetic granules embedded in the porous matrix. A magnetic particle may suitably comprise about 5-15 wt. % of the magnetic granules. The magnetic granules embedded in the porous matrix of each magnetic particle may have a volume-weighted median diameter (d50, v) of from about 1 to about 5 μm. Further, a magnetic particle may suitably comprise a concentration of magnetic granules in a central region of the magnetic particle of at least 200% of the concentration in a surface region of the magnetic particle, wherein the central region is defined as having a distance of >0.2 particle radii from the magnetic particle's surface and the surface region is defined as having a distance of <0.2 particle radii from the magnetic particle's surface.

Magnetic particles for use in the presently disclosed method comprise ligands capable of binding the biomolecule. The ligands may be covalently coupled to the porous matrix of the magnetic particles. It is to be understood that the type of ligand and its affinity constant $k_{off}/k_{on}$ towards the biomolecule is chosen based on the type of biomolecule which is to be separated from a cell culture or a biological solution. Further, it is to be understood that the concentration of ligand(s) per magnetic particle is dependent on or interrelated with, for example, the concentration of biomolecule in the cell culture or in the biological solution, the dimensions of the magnetic particles and/or the total volume of magnetic particles added to the magnetic separator.

In a currently preferred embodiment of the disclosure, the magnetic particles used in the presently disclosed method for separating a biomolecule are Mag Sepharose™ PrismA (GE Healthcare Bio-Sciences AB, art. no. 17550000).

Figure 2:
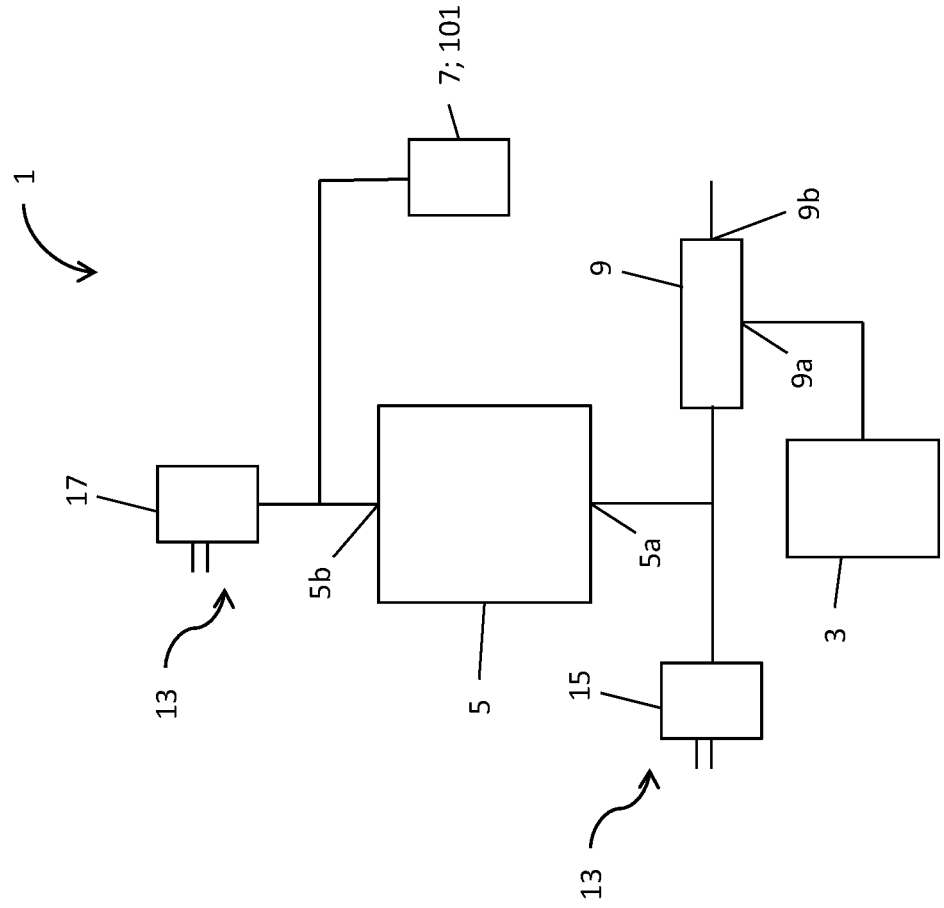
FIG. 2 schematically shows a system suitable for use in the presently disclosed method.

FIG. 2 schematically shows a non-limiting example of a separation system 1, which may be used to perform the method according to the present disclosure. The system 1 comprises a magnetic separator 5. The term "magnetic separator" has its conventional meaning in the field of separation processes, and refers to an apparatus which separates magnetic particles from a fluid. In a currently preferred embodiment of the present disclosure, the magnetic separator used in the method for separating a biomolecule is a high gradient magnetic separator, alternatively called a high gradient magnetic separation system (HGMS), as described in U.S. Pat. No. 7,506,765 B2, which is hereby incorporated by reference in its entirety. Parts of the separation system 1 shown in FIG. 2 are similar to parts of a system described in WO2018122246, which is hereby incorporated by reference in its entirety. The magnetic separator 5 comprises an inlet 5a for receiving a feed from a cell culture 3 or a biological solution 3 comprising said biomolecule and for receiving magnetic particles comprising ligands capable of binding this biomolecule. The magnetic separator 5 is configured for separating said magnetic particles with said bound biomolecule from the rest of the feed. The magnetic separator 5 comprises parts of magnetic or magnetizable material inside the magnetic separator which parts attract the magnetic particles when a magnetic field is applied.

The separation system 1 shown in FIG. 2 comprises a capturing cell 9 which is connected to the inlet 5a of the magnetic separator 5. The capturing cell 9 shown in FIG. 2 comprises a cell culture/biological solution inlet 9a for receiving a feed from a cell culture 3 and at least one magnetic particle inlet 9b for receiving magnetic particles. The capturing cell 9 is configured for mixing the feed from the cell culture or the biological solution and the magnetic particles thus allowing the target biomolecule to bind to the magnetic particles before forwarding it to the magnetic separator 5. However, it is to be understood that the capturing cell 9 is an optional component of the system 1. The cell culture 3, or the biological solution 3, could equally well function as a capturing cell if magnetic beads are added to the cell culture 3 or the biological solution, respectively, followed by providing a feed from the mixture of the cell culture and the magnetic particles, or from a mixture of the biological solution and the magnetic particles, respectively, comprising the bound biomolecule to the magnetic separator 5. Another alternative would be to add magnetic beads directly to the magnetic separator 5 instead. Separate addition of cell culture or biological solution, respectively, and magnetic beads directly into the magnetic separator is possible for all the embodiments.

Accordingly, step (b) of the presently disclosed method may comprise:

(i) adding the magnetic particles to a magnetic separator, followed by providing a feed from the cell culture or the biological solution to the magnetic separator, or
  (ii) providing a feed from a mixture of the cell culture and the magnetic particles, or from a mixture of the biological solution and the magnetic particles, comprising the bound biomolecule to the magnetic separator.

It is to be understood that after step (b), i.e. contacting the cell culture or the biological solution comprising the biomolecule with the magnetic particles to bind the biomolecule to the magnetic particles, the magnetic particles referred to in steps (c), (d) and (e) comprise the bound biomolecule.

According to step (d) mentioned above, the presently disclosed method may optionally comprise washing the magnetic particles with a washing liquid. For this purpose, the magnetic separator 5 is preferably connected to a washing arrangement 13 configured for washing out other components from the magnetic separator 5 than those magnetically bound to the parts of magnetic material. The washing arrangement 13 comprises at least one wash buffer providing arrangement 15 connected to a pump and to the inlet 5a of the magnetic separator possibly via a capturing cell 9 and a wash buffer collection arrangement 17 connected to an outlet 5b of the magnetic separator 5. The washing arrangement 13 is configured for flowing washing buffer through the magnetic separator 5 for washing out other components of the feed than those bound to the magnetic parts.

According to the presently disclosed method, the magnetic beads may be washed in batch mode in the magnetic separator, which is configured for releasing the magnetic field when the magnetic particles are to be washed in batch mode. Alternatively, and advantageously, the above-described method comprises applying at least one washing step in continuous mode, in which case step (d) of the above-described method comprises the following substeps:

(d1) agitating the magnetic particles in at least one plane to form a fluidised bed of magnetic particles, and (d2) providing a flow of a washing liquid in a direction essentially perpendicular to the at least one plane to remove the cell culture or the biological solution while retaining the magnetic particles in the magnetic field.

Herein, the phrase "essentially perpendicular to the at least one plane" is to be interpreted as meaning at an angle of 80-90° to the at least one plane.

Further, step (d) of the presently disclosed method may comprise the following substeps:

(i) removing the magnetic field;

(ii) resuspending the magnetic particles;

(iii) contacting the magnetic particles with a portion of washing liquid;

(iv) retaining the magnetic particles with a magnetic field; and (v) removing the washing liquid from the retained magnetic particles.

Alternatively or additionally, step (d) of the presently disclosed method may be repeated at least once, such as 1, 2, 3 or more times, before proceeding to step (e), or alternatively to step (e1).

The system 1 as shown in FIG. 2 further comprises a collection cell 7 for collecting eluate and waste. It is to be understood that in step (f) of the presently disclosed method, a flow of elution liquid is provided through the magnetic separator 5 by allowing the elution liquid to enter the magnetic separator 5 via the inlet 5a and by allowing the elution liquid to exit the magnetic separator 5 via the outlet 5b. The eluted biomolecule exits the magnetic separator 5 together with the elution liquid and may be collected in a collection cell 7 connected to the outlet 5b of the magnetic separator 5.

Consequently, the presently disclosed method may optionally further comprise a step (g) after step (f), comprising collecting the eluted biomolecule, which is exiting the magnetic separator with the elution liquid, in a collection cell, while retaining the magnetic particles with the magnetic field in the magnetic separator. The collection cell is connected to the outlet of the magnetic separator.

According to an alternative embodiment, instead of a collection cell 7, the system 1 as shown in FIG. 2 comprises a membrane chromatography device 101 for further purification, also called polishing, of the biomolecule. In this embodiment, in step (e1) of the presently disclosed method, a flow of elution liquid is provided through the magnetic separator 5 by allowing the elution liquid to enter the magnetic separator 5 via the inlet 5a and by allowing the elution liquid to exit the magnetic separator 5 via the outlet 5b. The eluted biomolecule exits the magnetic separator 5 together with the elution liquid and may be further purified, by separation from impurities and/or contaminants, in the membrane chromatography device 101 connected to the outlet 5b of the magnetic separator 5.

It is to be understood that in the system 1 shown in FIG. 2, the cell culture 3 or the biological solution 3, the magnetic separator 5 and the collection cell 7, or alternatively the membrane chromatography device 101, may be connected by pre-sterilized, flexible tubing and aseptic connectors. Furthermore, the collection cell 7, or alternatively the membrane chromatography device 101, can be pre-sterilized and disposable. A closed and sterile separation system for single use can hereby be provided.

The magnetic separator used to perform the presently disclosed method further comprises an agitating arrangement (not shown in FIG. 2; one non-limiting example shown in FIG. 3 as described further below). The agitating arrangement is configured to apply an agitating motion to the magnetic particles, to make the magnetic particles move around in a plane perpendicular to the direction of the flow through the magnetic separator. The agitating arrangement may comprise at least one component, such as a plurality of components, configured for varying the magnitude of the magnetic field, such as by applying an oscillating magnetic field, i.e. varying the magnitude in a regular manner around a central point or plane. Thus, step (e), or alternatively step (e1), of the presently disclosed method may comprise agitating the magnetic particles by varying the magnitude of the magnetic field in at least one plane of the magnetic separator, such as by applying an oscillating magnetic field in at least one plane of the magnetic separator. Alternatively, the agitating arrangement may comprise at least one agitator, such as a plurality of agitators, in which case step (e), or alternatively step (e1), of the presently disclosed method comprises agitating the magnetic particles by applying, or switching on, the agitator(s). Herein, the term "agitator" refers to any type of device or substance/material capable of agitating, such as rotating or stirring, magnetic particles in the magnetic separator. Non-limiting examples of suitable agitators are devices such as rotatable separation structures, such as rotatable discs or rotatable blades, being attached to at least one fixed structure of the magnetic separator, such as being mounted on a central rotatable carrier shaft forming a rotor. The separation structures may for example consist of a wire mesh, a perforated metal foil or a perforated metal sheet.

Advantageously, the agitators may comprise magnetizable material, in which case the agitators may act as the parts of magnetic material inside the magnetic separator, which parts attract the magnetic particles when a magnetic field is applied.

Figure 3:
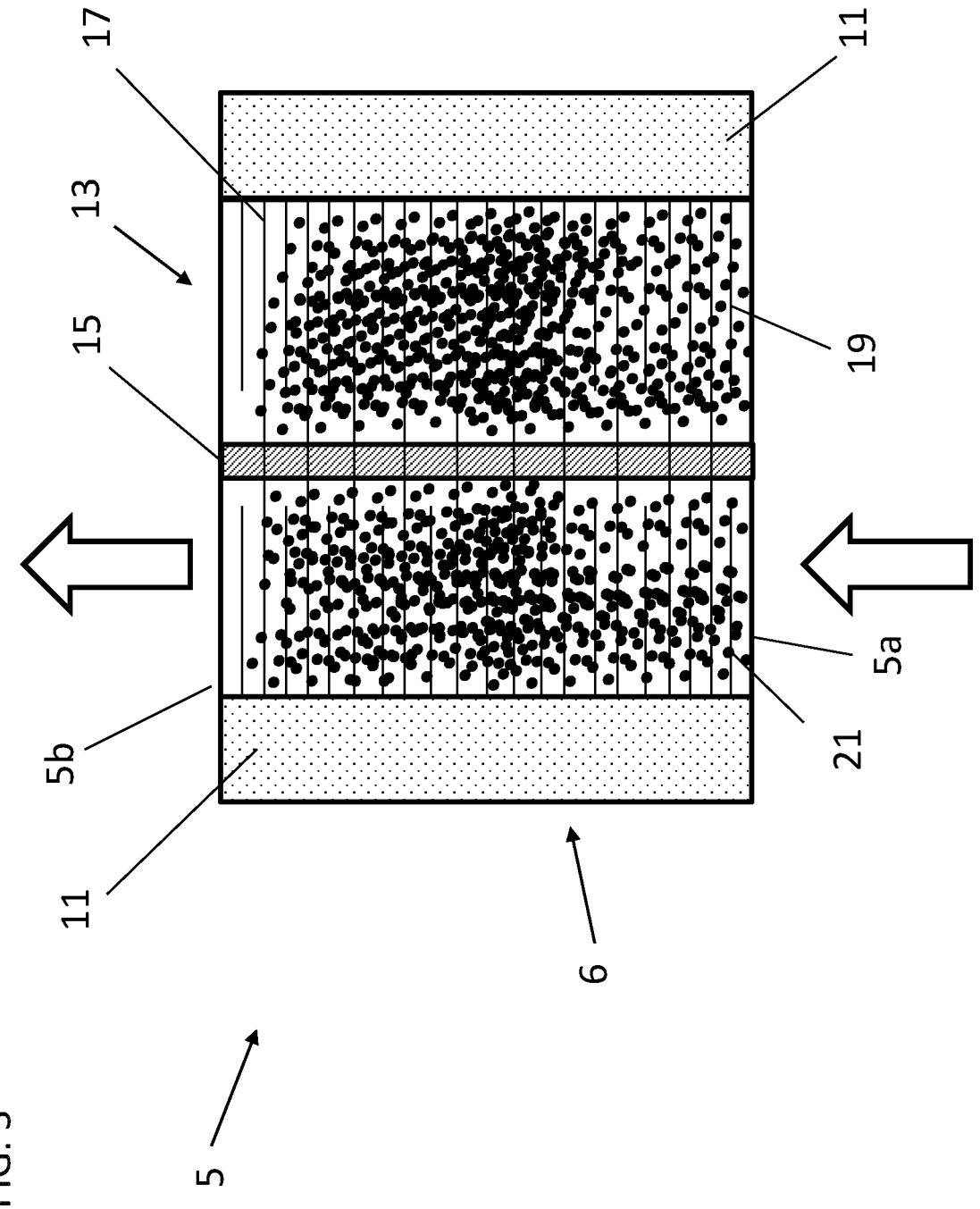
FIG. 3 is a schematic drawing of a non-limiting embodiment of a magnetic separator suitable for use in the presently disclosed method.

FIG. 3 schematically shows a cross-sectional view of a non-limiting example of a magnetic separator 5 which may be used to perform the method according to the present disclosure. The arrows in FIG. 3 illustrate a flow of liquid (e.g. elution liquid) which may enter the magnetic separator 5 at the inlet 5*a* and exiting the magnetic separator 5 at the outlet 5*b*. The magnetic separator 5 comprises a housing 6, and further comprises a hollow, cylindrical electro magnet 11 configured to create a magnetic field in the magnetic separator when the electro magnet is turned on. The magnetic separator further comprises an agitating arrangement 13 comprising a rotor 15 on which a plurality of rotatable discs 17 are mounted. The agitating arrangement 13 is configured for agitating the magnetic particles 21 in at least one plane of the magnetic separator 5 to form a fluidised bed of magnetic particles in the magnetic separator, in accordance with step (e), or alternatively step (e1), of the presently disclosed method. In FIG. 3, the magnetic separator 5 further comprises a plurality of stationary discs 19 mounted on the housing 6. The rotatable discs 17 and the stationary discs 19 are arranged alternately in the housing 6. The rotatable discs 17 and/or the stationary discs 19 may comprise magnetizable material. Further, the rotatable discs 17 and/or the stationary discs 19 may be perforated to allow magnetic particles and cell culture/biological solution to pass through the discs. It is to be understood that the configuration of the rotatable discs and/or the configuration of the stationary discs may be different from the configuration shown in FIG. 3. For example, the stationary discs 19 may be connected to the rotor 15, e.g. by means of sealing material. Further, the rotatable discs may or may not be connected to the wall of the housing 6. It is further to be understood that the agitating arrangement may comprise other components than those shown in FIG. 3. For example, instead of or in addition to having parts of magnetizable material being attached to a fixed structure of the magnetic separator, it is contemplated to include parts of magnetic or magnetizable material inside the magnetic separator which are not attached to any fixed structure of the magnetic separator, such as a wad or flock of steel wool or wire wool, and which attract the magnetic particles when a magnetic field is applied and which have a capacity to retain the magnetic particles in the magnetic field in the magnetic separator.

Step (e), or alternatively step (e1a), of the presently disclosed method may comprise agitating the magnetic particles in at least one plane, such as in a plurality of essentially parallel or parallel planes, of a magnetic separator to form a plurality of fluidised beds of magnetic particles. Herein, "essentially parallel planes" is to be interpreted as planes being arranged at an angle of 0-10° in relation to each other. In the case of a plurality of essentially parallel or parallel planes, step (f), or alternatively step (e1b) comprises providing the flow of an elution liquid in a direction essentially perpendicular or perpendicular to the plurality of planes. Without wishing to be bound by theory, it is believed that if the agitating arrangement comprises a plurality of agitators in the form of rotatable components, arranged in parallel within the magnetic separator, and configured to agitate the magnetic particles in a plurality of parallel planes; it is possible to form a fluidised bed between every pair of agitators.

In the presently disclosed method, the speed of the agitator(s) in step (e), or alternatively in step (e1), may be in a range of from 15 to 1500 rpm, such as 15, 20, 30, 40, 50, 100, 150, 200, 300, 400, 500, 600, 700, 800, 900, 1000, 1100, 1200, 1300, 1400, or 1500, preferably in a range of from 50 to 300 rpm.

According to an alternative embodiment, the above-described steps (f) and (g), following step (e), are replaced by steps (f1) and (g1), following step (e1), comprising:

(f1) forwarding the biomolecule eluted from the magnetic separator to a membrane chromatography device;

(g1) separating the biomolecule from impurities and/or contaminants by membrane chromatography.

The location of the membrane chromatography device 101 in the system 1 according to FIG. 2 has been described above. Step (g1) may alternatively be called polishing of the biomolecule.

The term "membrane chromatography" has its conventional meaning in the field of bioprocessing. In membrane chromatography there is binding of components of a fluid, for example individual molecules, associates or particles, to the surface of a solid phase in contact with the fluid. The active surface of the solid phase is accessible for molecules by convective transport. The advantage of membrane adsorbers over packed chromatography columns is their suitability for being run with much higher flow rates. This is also called convection-based chromatography. A convection-based chromatography matrix includes any matrix in which application of a hydraulic pressure difference between the inflow and outflow of the matrix forces perfusion of the matrix, achieving substantially convective transport of substance(s) into the matrix or out of the matrix, which is effected very rapidly at a high flow rate. Convection-based chromatography and membrane adsorbers are described in for example US20140296464A1, US20160288089A1, WO2018011600A1, WO2018037244A1, WO2013068741A1, WO2015052465A1, US786778482, hereby incorporated by reference in their entireties.

In the presently disclosed method, the membrane chromatography device may comprise a chromatography material comprising one or more electrospun polymer nanofibres which in use form a stationary phase comprising a plurality of pores through which a mobile phase can permeate. The stationary phase may be in the form of a membrane.

Alternatively, the membrane chromatography device may comprise at least one adsorptive membrane. The adsorptive membrane may comprise polymer nanofibres. Optionally, the membrane, e.g. an adsorptive membrane, may comprise a nonwoven web of polymer nanofibres.

The polymer nanofibers may have mean diameters from 10 nm to 1000 nm. For some applications, polymer nanofibers having mean diameters from 200 nm to 800 nm are appropriate. Polymer nanofibers having mean diameters from 200 nm to 400 nm may be appropriate for certain applications.

The chromatography material or the membrane, e.g. an adsorptive membrane, may comprise a polymer selected from the group consisting of polysulfones, polyamides, nylon, polyacrylic acid, polymethacrylic acid, polyacrylonitrile, polystyrene, and polyethylene oxide, and mixtures thereof. Alternatively, or additionally, the polymer may be a cellulosic polymer, such as selected from a group consisting of cellulose and a partial derivative of cellulose, particularly cellulose ester, e.g. cellulose acetate, cross-linked cellulose, grafted cellulose, or ligand-coupled cellulose.

In the presently disclosed method, the membrane chromatography device may comprise a chromatography material functionalised with (i) a positively charged group, such as a quaternary amino, quaternary ammonium, or amine group, or (ii) a negatively charged group, such as a sulfonate or carboxylate group. Alternatively, or additionally, the membrane chromatography device may comprise a chromatography material functionalised with a multimodal ligand selected from a group consisting of a multimodal anion exchange ligand and multimodal cation exchange ligand. The multimodal anion exchange ligand may be a N-benzyl-N-methyl ethanol amine ligand coupled to a support, wherein said support is linked to the nitrogen atom of the ligand through a linker. Alternatively, or additionally, the membrane chromatography device may comprise a chromatography material functionalised with (i) an ion exchanger group, (ii) an affinity peptide/protein based ligand, (iii) a hydrophobic interaction ligand, (iv) an IMAC ligand, or (v) a DNA based ligand such as Oligo dT.

In order to increase surface area and capacity with convection based membrane adsorbers, the size of convective pores of the convective matrix may be reduced, such as by use of nanofibres as mentioned above. As a result, resistance to flow will increase, however. Therefore, high flow rates through a chromatography device comprising a convective matrix of high capacity will require a chromatography device and design which can withstand high operating pressures.

In an embodiment of the presently disclosed method involving membrane chromatography, one may use a membrane chromatography device as described in detail in the previously filed patent application IN 201911019289, internal reference no. 502800-IN-1, hereby incorporated by reference in its entirety.

Figure 7:
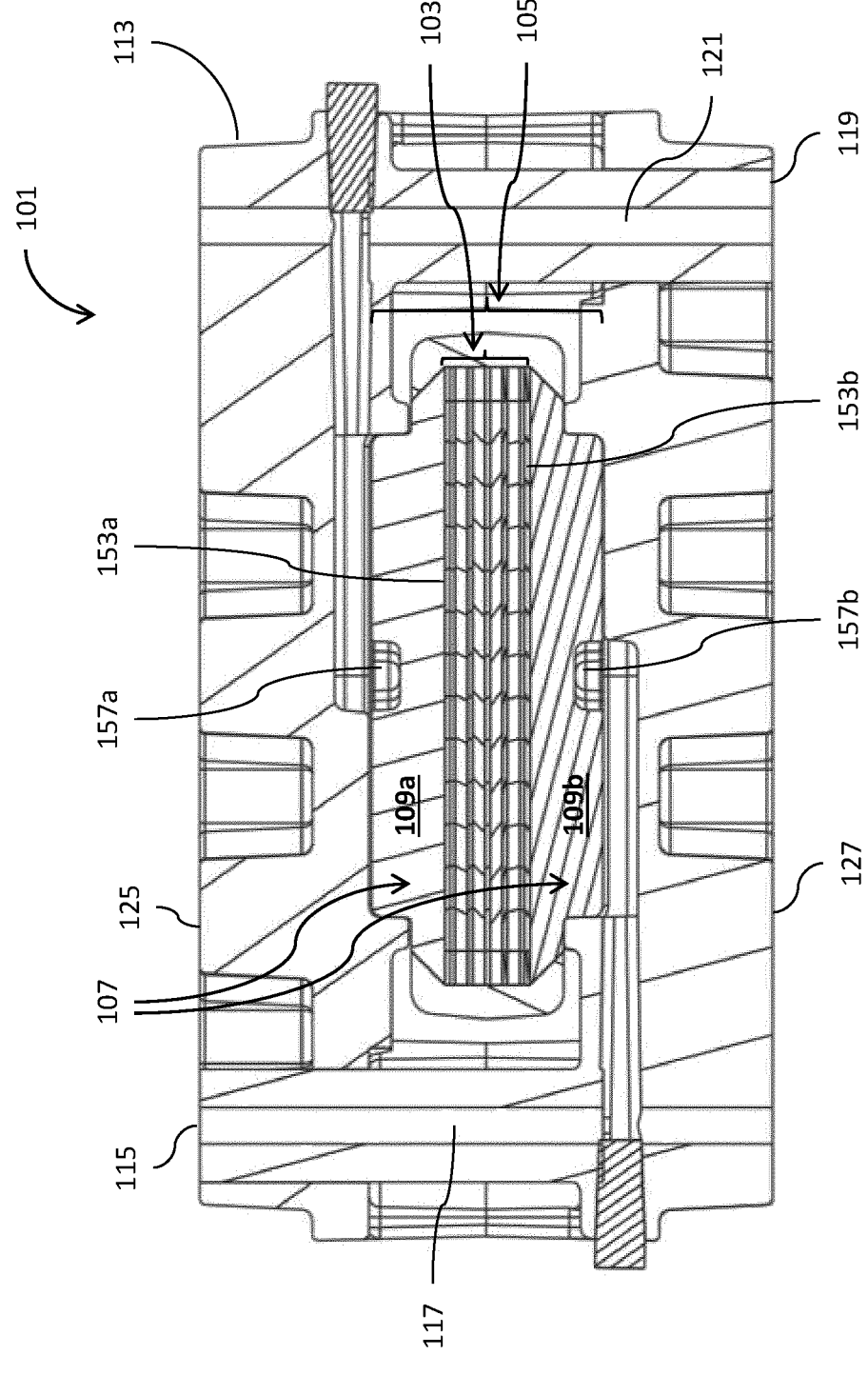
FIG. 7 is a cross section of a membrane chromatography device which may be used according to one embodiment of the alternative method for separating a biomolecule according to the present disclosure.

As illustrated in FIG. 7, the membrane chromatography device 101 comprises a chromatography material unit 103 which is provided within a cassette 105. The membrane chromatography device 101 further comprises a fluid distribution system 107 which is configured to distribute fluid into and out from the at least one chromatography material unit 103. The chromatography material unit 103 is sandwiched between a distribution device 109a and a collection device 109b of the fluid distribution system 107 as described above. The distribution device 109a and the collection device 109b are identical in the embodiment shown in FIG. 7; however, this is not necessary. In the embodiment shown in FIG. 7, the cassette 105 comprises the chromatography material unit 103 and the fluid distribution system 107, in the form of a distribution device 109a and a collection device 109b. In another embodiment, said fluid distribution system 107 can be provided separately from the cassette 105, for example as a separate unit or integrated into a housing 113 of the chromatography device 101.

The membrane chromatography device 101 further comprises a housing 113 in which the at least one chromatography material unit 3 and the cassette 105 are provided. The housing comprises a top plate 125 and a bottom plate 127. An inlet 115 for receiving a fluid feed is provided in the top plate 125 and an outlet 119 for transferring a fluid outflow from the chromatography device is provided in the bottom plate 127. The top plate 125 and the bottom plate 127 are connected to each other such that an inlet fluid channel 117 is connecting the inlet 115 with the chromatography material unit 103 via the fluid distribution system 107 and an outlet fluid channel 121 is connecting the outlet 119 with the chromatography material unit 103 via the fluid distribution system 107.

The distribution device 109a of the fluid distribution system 107 may comprise a plate (not shown) which is provided abutting an inlet surface 153a of the chromatography material unit 103, wherein said plate comprises a number of openings for distributing a fluid feed provided from the inlet 115 of the chromatography device 101 to the chromatography material unit 103, wherein a total area of said openings in the plate is smaller than the rest of the area of the plate or less than 20% or less than 10% of the rest of the area of the plate, wherein said openings are connected to a distribution device inlet 157a via one or more fluid conduits (not shown) provided in the distribution device 109a.

Further, the collection device 109b of the fluid distribution system 107 may comprise a plate (not shown) which is provided abutting an outlet surface 153b of the chromatography material unit 103, wherein said plate comprises a number of openings for collecting a fluid from the chromatography material unit 103, wherein a total area of said openings in the plate is smaller than the rest of the area of the plate or less than 20% or less than 10% of the rest of the area of the plate, wherein said openings are connected to a collection device outlet 157b via one or more fluid conduits (not shown) provided in the collection device 109b.

The at least one chromatography material unit 103 may comprise at least one adsorptive membrane, and/or any one or several of the chromatography materials described elsewhere herein. The least one chromatography material unit may comprise at least one adsorptive membrane sandwiched between at least one top spacer layer (not shown) and at least one bottom spacer layer (not shown), or may comprise at least two adsorptive membranes stacked above each other and interspaced with spacer layers (not shown) and sandwiched between at least one top spacer layer and at least one bottom spacer layer.

At least some parts of said chromatography device 101 may be sealed together, leaving at least the inlet 115 and the outlet 119 open. In some embodiments, at least some parts of said chromatography device 101 may be sealed together by plastic or elastomer. Alternatively, or additionally, at least some parts of said chromatography device 101 may be overmolded and sealed together. Further, the cassette 105 and/or the housing 113 may be overmolded. The overmolding is a process for creating a seal and for providing stability to the device, thereby providing a robust membrane chromatography device 101. After the overmolding, the chromatography device 101 can withstand an operating pressure of at least 10 bar or at least 15 bar.

In step (f) or alternatively step (e1b), of the presently disclosed method, the linear flow rate in the direction essentially perpendicular to the at least one plane, or alternatively essentially perpendicular to the plurality of planes, is in a range of from 10 to 3000 cm/h, preferably in a range of from 50 to 600 cm/h. A similar flow rate may be applied where relevant in other steps of the presently disclosed method, i.e. a flow rate in a range of from 10 to 3000 cm/h, preferably in a range of from 50 to 600 cm/h, such as in, but not limited to, step (d), step (e) or alternatively step (e1), and/or step (g) or alternatively step (f1) and/or step (g1).

In step (g1) of the presently disclosed method, the residence time of the biomolecule in the membrane chromatography device may be in a range of from about 0.5 s to about 6 min, preferably from about 1 s to about 30 s. This equals that the residence time of the biomolecule in the membrane or chromatography material may be in a range of from about 0.5 s to about 6 min, preferably from about 1 s to about 30 s.

Consequently, the flow rate of elution liquid through the membrane chromatography device may be in a range which corresponds to a residence time in the membrane chromatography device in step (g1) which is in a range of from about 0.5 s to about 6 min, preferably from about 1 s to about 30 s.

The flow of elution liquid through the membrane or chromatography material may be a normal flow or a tangential flow.

Further, the membrane chromatography in step (g1) may be flow-through membrane chromatography.

The presently disclosed method may further comprise performing, between step (e1) and step (f1), an adjustment of the pH of the elution liquid, a dilution of the elution liquid, or an adjustment of the conductivity of the elution liquid. In the presently disclosed method, at least steps (c)-(f) or alternatively steps (c)-(e1), such as steps (b)-(f) or alternatively steps (b)-(e1), may be performed in the magnetic separator.

Alternatively, steps (b)-(f), or steps (b)-(e1), respectively, may be carried out in a system comprising a bioreactor vessel being fluidically connected to a contactor and the contactor being fluidically connected to the magnetic separator. The bioreactor vessel comprises the cell culture/biological solution before starting the separation of biomolecule from the cell culture/biological solution. The contacting of the magnetic particles with the cell culture/biological solution may be performed in the contactor, which may be a vessel to which the cell culture/biological solution and the magnetic particles are conveyed (e.g. pumped, entrained by a liquid stream or fed by gravity) and which may be agitated to some extent to provide rapid mass transport into the magnetic particles. The bioreactor vessel or the contactor may e.g. be a flexible bag, such as a flexible plastic bag with one or more inlet and outlet ports.

The separation system used in the presently disclosed method may further comprise a pressurizing arrangement, for example a peristaltic pump, configured to create the flow through the magnetic separator. Alternatively, the flow through the magnetic separator may be created solely by gravity. In general, the pressure applied in the system to make the presently disclosed method work may be much lower than the pressure applied in a high-pressure liquid chromatography (HPLC) system. Advantages associated herewith include simpler construction and lower costs. A non-limiting example of a suitable range of pressures to be applied to the separation system is 0-0.5 bar, such as 0.01-0.5 bar.

In the presently disclosed method, the magnetic separator may be connected to a chromatography system (i.e. replacing a chromatography column in a chromatography system), such as an ÄKTA™ Pilot system (GE Healthcare). Although the pump pressure performance of the chromatography system is not needed, it may be convenient to use the buffer control features, including dual pumps for gradient generation, the valving and the detector of the chromatography system.

The system, and/or the magnetic separator and/or the membrane chromatography device therein, used in the presently disclosed method may be configured for automatic, semi-automatic or manual operation. It can be used in both pilot and manufacturing scale processes, with amounts of magnetic particles at least in the interval from 0.1 L to 10 L. It is applicable in particular to capture of biopharmaceuticals from non-clarified feeds such as cell cultures, biological solutions, or cell lysates. Devices "comprising" one or more recited elements may also include other elements not specifically recited. The term "comprising" includes as a subset "consisting essentially of" which means that the device has the components listed without other features or components being present. Likewise, methods "comprising one or more recited steps may also include other steps not specifically recited.

The singular "a" and "an" shall be construed as including also the plural.

The magnetic separator used in the following examples is a High Gradient Magnetic Separation system (HGMS), more particularly a MES 100 RS (Andritz KMPT GmbH). However, it is to be understood that any type of magnetic separator being configured as described in detail above may be used for performing the presently disclosed method.

Equally, it is to be understood that any type of membrane chromatography device having a design which can withstand high operating pressures, as mentioned above, may be used for performing the presently disclosed method, thus not being limited to a cellulose fiber chromatography (known as Fibro chromatography) cassette/unit, as used in some of the examples below. The Fibro chromatography (GE Healthcare Life Sciences) is an ultrafast chromatography purification for short process times and high productivity, which utilizes the high flow rates and high capacities of cellulose fiber.

Further, the membrane chromatography material to be used in the membrane chromatography device is not limited to the so-called Fibro adhere material, as used in some of the following examples. The Fibro adhere (GE Healthcare Life Sciences) is a material comprising cellulose nanofibres, which may be derivatised with a strong ion exchange multimodal ligand. Another non-limiting example of a suitable membrane chromatography material is Capto™ adhere (GE Healthcare Life Sciences), which is based on a rigid agarose matrix that allows high fluid velocities to be used. The agarose matrix is derivatised with a multimodal anion exchange ligand, N-benzyl-N-methylethanolamine.

Example 1

Purpose

The purpose of this study was to bind and elute IgG using Mag Sepharose™ PrismA and a High Gradient Magnetic Separator (HGMS) system, MES 100 RS (Andritz KMPT GmbH). The purpose was to see if it was possible to elute IgG from the HGMS system using flow elution.

Materials
- Polyclonal IgG (Gammanorm™), Octapharma
- $NaH_2PO4$ $H_2O$, pa, Merck
- $Na_2HPO4$ 2 $H_2O$, pa, Merck
- Na-acetate trihydrate, pa, Merck
- Acetic acid, pa, Merck
- Tween™ 20, Merck
- Tris base, pa, Merck
- Mag Sepharose™ PrismA, GE Healthcare Equipment
- HGMS Equipment, MES 100 RS, Andritz KMPT GmbH
- 25 L plastic buffer trays
- Mixing rotor, RW20, Janke & Kunkel
- 125 mL sterile plastic bottles, Nalgene
- Spectrophotometer, GENESYS™ 10S UV-Vis, Thermo Scientific
- Glass filter, G3, ~700 ml, Scott Duran
- Centrifuge, 5810R, Eppendorff Buffers
20 mM Na-Phosphate+0.15 M NaCl pH 7.4
11.35 g Na $NaH_2PO_4 \cdot H_2O$, 74.3 g $Na_2HPO_4$ and 219.2 g NaCl was diluted and mixed with 25 L $dH_2O$ in a 25 L buffer container.

100 mM NaOAc pH 3.2

140 mL acetic acid and 7.4 g NaOAc. 3H$_2$O was diluted and mixed with 25 L dH$_2$O in a 25 L buffer container.

1 M NaOH 40 g NaOH was diluted and mixed with 1000 mL milliQ water.

PBS with 0.05% Tween

Two tablets of PBS from Medicago was mixed with 2000 mL MilliQ water. 1 mL Tween 20 was pipetted and mixed with the solution.

100 mM NaOAc pH 2.9

5.7 mL Acetic acid and 0.02 g NaOAc 3H$_2$O was mixed with 1000 mL milli-Q water.

Protocol

Preparation of Mag Sepharose PrismA 200 mL Mag Sepharose PrismA was washed with 5 cv PBS on a glass filter (G3 pore size) prior use.

Preparation of IgG, 2 mg/ml in 6 L 12 g (73 ml of 165 mg/ml) Human IgG, Gammanorm was diluted in 6L of 20 mM M NaCl pH 7.4. The total volume was 6080 ml and the IgG concentration was analyzed with UV280 to 1.9 mg/ml.

Incubation of Mag Sepharose PrismA 37-100 with IgG

The 400 mL of the washed beads were transferred into a bucket with the 6 L solution with IgG and mixed for one hour.

HGMS Process

The cooling water, air pressure and distilled water was turned on the MES 100 RS system. The peristaltic pump of the system was first calibrated with water to fill 1 L volumetric flask at room temperature to wash the tubes and remove air from the system, and then with the prepared buffers.

TABLE 1

| Calibration of peristaltic pump | |
| --- | --- |
| % speed of pump | Flow (L/min) |
| 5 | 0.14 |
| 10 | 0.29 |
| 20 | 0.58 |
| 30 | 0.87 |
| 40 | 1.16 |
| 50 | 1.45 |
| 60 | 1.73 |
| 70 | 2.02 |
| 80 | 2.31 |
| 90 | 2.6 |
| 100 | 2.89 |

After incubation, the following program was used on the magnetic separator:

2 GE-IgG-purif:

Main Step 1: Load Magnetic Particles (MP)

Sub1: load: stop all before start, step time 250 sec, magnet on, pump set value+50%, open valve XV01 and XV14.

The remaining feed was pumped in manually using PBS buffer to wash the tube.

Main Step 2: recirculate

Sub1: recirculate: Step time 30 sec, Magnet on, Pump set value+30%, open valve XV08 and XV13.

Main Step 3: wash buffer

Sub1: feed buffer 1: Step time 60 sec, Magnet on, Pump set value+70%, open valve XV02 and XV14.

Sub2: mix buffer: Stop all before start, step time 20 sec, Mixer set value 60%

Sub3: trap: Step time 10 sec, Magnet on,

Sub4: recapture: Step time 60 sec, Magnet on, Pump set value+30%, open valve XV08 and XV13.

Sub5: transition: Step time 1 sec, Magnet on, open valve XV02, XV08 and XV13 and XV14.

Main Step 4: wash H$_2$O

Sub1: feed buffer 2: Step time 60 sec, Magnet on, Pump set value+70%, open valve XV03 and XV14.

Sub2: mix buffer 2: Stop all before start, step time 20 sec, Mixer set value 60% Sub3: trap: Step time 10 sec, Magnet on, Sub4: recapture: Step time 60 sec, Magnet on, Pump set value+30%, open valve XV08 and XV13.

Sub5: transition: Step time 1 sec, Magnet on, open valve XV02, XV08 and XV13 and XV14.

Main Step 5: elution

Sub1: trap: Step time 10 sec, Magnet on

Sub2: recap: Step time 60 sec, Magnet on, Pump set value+30%, open valve XV08 and XV13.

Sub3: transition: Step time 1 sec, Magnet on, open valve XV07, XV08 and XV13 and XV16.

Sub4: feed eluate: Step time 4200 sec, Magnet on, Mixer set value 10%, Pump set value+5%, open valve XV07 and XV16.

The eluate was collected in ~100 ml fractions by hand in pre-weight 125 ml plastic bottles. After elution each bottle was weighed and the actual elution volume in each bottle was determined by subtracting the total volume with the empty bottle volume (51.5 mg).

Analysis

The eluates were neutralized to pH 5 with 2 M tris base. Titer was determined in all fractions by UV280 using a Spectrophotometer, GENESYS from ThermoFisher.

Results, Analysis and Conclusions

The concentration was calculated by dividing the UV280 value in a 1 cm cuvette with the extinction coefficient 1.36 to obtain the concentration in mg/ml of IgG. The samples were diluted if the UV280 value was above 1. The concentration and cumulative yield were plotted against the cumulative volume of the elution.

Figure 4:
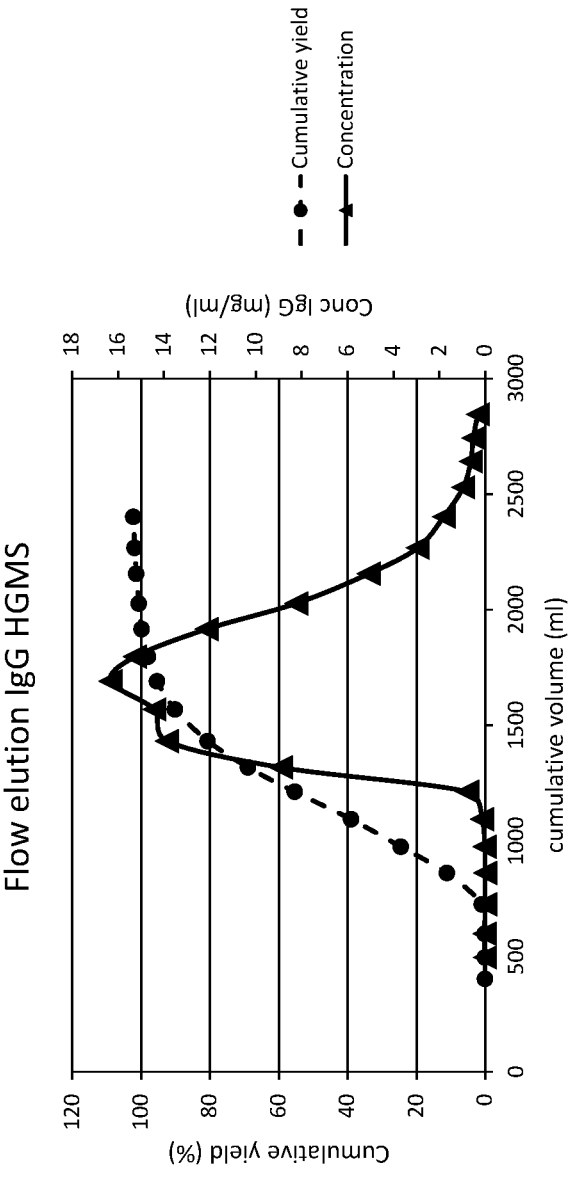
FIG. 4 is a graph showing the elution curve from a polyclonal IgG experiment described in Example 1 below.

The graph in FIG. 4 shows a distinct elution peak with a yield of 98% with 2.7×CV (the total magnetic bead volume of 0.4 L).

CONCLUSION

The mixing and flowrate was set such that no magbeads were coming out from the magnetic chamber during the elution. The mixing while having the magnet switched on at the same time will cause the magbeads to be suspended in the magnetic chamber allowing a continuous elution instead of batch elution of the IgG.

This experiment shows that it is possible to elute IgG in a continuous mode while mixing in the magnetic chamber with Mag Sepharose Prisma 37-100 μm, resulting in a 98% yield in 2.7 volumes of Mag Sepharose beads.

Example 2

Purpose

The purpose of this study was to clarify and purify a CHO cell culture with an IgG1 monoclonal antibody using Mag Sepharose PrismA (37-100 μm) and a High Gradient Magnetic Separator (HGMS) system, MES 100 RS (Andritz KMPT GmbH). The purpose was to see if it was possible to elute the mAb from the HGMS system using flow elution without losing any Mag Sepharose.

Materials

CHO cell culture, GE Healthcare $NaH_2PO_4$ $H_2O$, pa, Merck $Na_2HPO_4$ 2 $H_2O$, pa, Merck Na-acetate trihydrate, pa, Merck Acetic acid, pa, Merck Tween 20, Merck Tris base, pa, Merck Mag Sepharose PrismA, 37-100 μm, GE Healthcare mAb standard, 8.82 mg/mL, GE Healthcare Equipment HGMS Equipment, MES 100 RS, Andritz KMPT GmbH 25 L plastic buffer trays Mixing rotor, RW20, Janke & Kunkel 125 mL sterile plastic bottles, Nalgene HPLC, 1260 Infinity, Agilent Technologies Glass filter, G3 pore size, ~700 mL, Scott Duran Centrifuge, 5810R, Eppendorff pH meter, 913 pH meter, Metrohm MabSelect SuRe HiTrap, 29-0491-04, GE Healthcare Superdex 200 Increase 10/300 GL, GE Healthcare 0.2 μm syringe filters, Sterivex HV, Millipore 10-100 μL pipette Mettler Toledo 100-1000 μL pipette Eppendorff Cellbag™ 10 L, BC11, Basic, GE Healthcare Conditions and Observations Preparation of Solutions:

20 mM Na-Phosphate+0.15 M NaCl pH 7.4

11.35 g Na $NaH_2PO_4$·$H_2O$, 74.3 g $Na_2HPO_4$ and 219.2 g NaCl was diluted and mixed with 25 L $dH_2O$ in a 25 L buffer container.

100 mM NaOAc pH 3.2

140 mL acetic acid and 7.4 g NaOAc·3·$H_2O$ was diluted and mixed with 25 L $dH_2O$ in a 25 L buffer container.

1 M NaOH 40 g NaOH was diluted and mixed with 1000 mL milliQ water.

PBS with 0.05% Tween

Two tablets of PBS from Medicago was mixed with 2000 mL MilliQ water. 1 mL Tween 20 was pipetted and mixed with the solution.

100 mM NaOAc pH 2.9

5.7 mL Acetic acid and 0.02 g NaOAc 3$H_2O$ was mixed with 1000 mL milli-Q water.

Preparation of mAb Feed

An amount of ~7 L of CHO cells containing mAb was used. Cell density was 23.81 MVC/mL, Viability: 66.4% and mAb titer 2.7 mg/mL. The cells were pumped into a 10 L cell bag (basic).

Preparation of Titer Analysis Method, MabSelect SuRe HiTrap Bind and Elute

A MabSelect SuRe HiTrap™ column was coupled onto the HPLC system. A standard curve with mAb (mAb titer 8.82 mg/mL) was prepared in 250 μL plastic HPLC vials according to the table below.

TABLE 2

| Preparation of standard curve mAb | | |
| --- | --- | --- |
| STD conc (mg/mL) | STD volume (μL) | PBS volume (μL) |
| 1 | 22.7 | 177.3 |
| 2 | 45.4 | 154.6 |
| 3 | 68.0 | 132.0 |
| 4 | 90.7 | 109.3 |
| 5 | 113.3 | 86.7 |

Description, MabSelect SuRe Hitrap Method (Titer with HPLC):

Injection volume: 50 μL

Flow: 1 mL/min

Detection: 280 nm

A-buffer: PBS+0.05% Tween pH 7.4

B-buffer: 100 mM NaOAc pH 2.9

TABLE 3

| Time scheme for HPLC method | |
| --- | --- |
| Time (min) | % A-buffer |
| 0 | 100 |
| 3 | 100 |
| 13 | 30 |
| 14 | 30 |
| 16 | 0 |
| 16.01 | 100 |
| 18 | 100 |
| 23 | 100 |

Titer Determination of Cell Culture

~10 mL cell suspension was centrifuged at 3000 rpm for 5 minutes and the volume cell debris (solids) was determined to 5% by monitoring the total volume cell suspension and total volume solids. Supernatant was filtrated through a 0.2 μm filter into a 1 mL HPLC vial. Titer of the supernatant was determined according to the titer method described above.

TABLE 4

| Standard curve mAb | |
| --- | --- |
| STD mAb (mg/mL) | Response (mAUs) |
| 0 | 0 |
| 1 | 3993 |
| 2 | 8545 |
| 3 | 13293 |
| 4 | 17301 |
| 5 | 22187 |

Titer mAb Cell Supernatant:

Response=11924 mAUs

Titer=11924/4383.7=2.72 mg/mL

Preparation of Mag Sepharose PrismA 400 mL Mag Sepharose PrismA was washed with 5 cv PBS on a glass filter (G3 pore size) prior use.

Incubation of Mag Sepharose PrismA with Cell Culture

The 400 mL washed beads were transferred into a bottle with 6250 g CHO cell suspension. The magnetic beads were mixed with the CHO cell suspension for one hour. One mL of sample was centrifuged and analysed with the mAbSelect SuRe Hitrap method (see above) to investigate remaining mAb in the feed (not bound to the Mag Sepharose PrismA).

HGMS Process

The cooling water, air pressure and distilled water was turned on the MES 100 RS system. The peristaltic pump of the system was calibrated with water to fill 1 L volumetric flask at room temperature.

The inlet tubes and valves to be used XV01, XV02, XV 03, XV 07 were primed with dH20. Air bubbles in the magnetic separator were removed by priming the system and at the same time turning on the mixer at 50%, until all air is removed. The hose between circulation valves XV08 and XV013 was filled until no air was present using back-flow in the system.

After water priming the system was primed with actual running buffers.

XV01=Mag bead mixture load (primed with 20 mM Naphosphate+0.15 M NaCl pH 7.4)

XV02=20 mM Na-phosphate+0.15 M NaCl pH 7.4

XV03=dH$_2$O

XV 07=100 mM Na-acetate pH3.2

After incubation the following program was used on the magnetic separator.

Step 1 Load Mixture of Magnetic Particles and Feed

The pumping time was set to 250 seconds to pump in 6 L feed mixture. Remaining feed was pumped in manually using PBS buffer to wash the inlet tube of the mixture.

The system was set to recirculation to trap all magnetic beads on the magnetizable discs in the separation unit.

Step 2 Wash with 20 mM Na-Phosphate+0.15 M NaCl, Repeated 4 Cycles

Sub step 1. Feed buffer for 60 s using 70% pump speed (2 L buffer).

Sub step 2. Mix buffer and beads for 20 s and 60% rotor speed, turning magnet and valves off.

Sub step 3. Trap the beads by turning on the magnet.

Sub step 4. Recapture. Recirculate to trap all beads using pump rate at 30%.

Sub step 5. Transition. Short (1 s) valves opening to avoid back pressure.

Step 3. Wash with Water, One Cycle

Same substeps were used at water wash as for the washings with 20 mM Na-Phosphate+0.15 M NaCl, except that water was pumped from valve XV03.

Step 4. Elution

In this step we flow-eluted the mAb using mixer on and magnet on.

Sub step 1. Trap. Turned magnet on.

Sub step 2. Recap. Recirculate for 60 sec using 30% pump speed.

Sub step 3. Transition. Opening of valves for short moment (1 s) to avoid back pressure.

Sub step 4. Feed eluate: Elution with 100 mM NaOAc pH 3.2, valve XV07. Magnet on, pump speed at 5% (140 mL/min), mixer set at 10%. Elution was made for 4286 s.

The eluted material was collected in ~100 mL fractions by hand in pre-weight plastic 150 mL bottles.

After elution each bottle was weighed and the actual elution volume in each bottle was determined by subtracting the total volume with the empty bottle volume. See table 5 below.

TABLE 5

Volumes of elution fractions

| Fraction | Volume (g, mL) |
|---|---|
| 4 | 115.51 |
| 5 | 111.22 |
| 6 | 89.7 |
| 7 | 102.61 |
| 8 | 97.7 |
| 9 | 92.7 |
| 10 | 99.25 |
| 11 | 107.55 |
| 12 | 115.19 |
| 13 | 109.14 |
| 14 | 112.26 |
| 15 | 109.22 |
| 16 | 125.24 |
| 17 | 114.47 |
| 18 | 121.98 |

TABLE 5-continued

Volumes of elution fractions

| Fraction | Volume (g, mL) |
|---|---|
| 19 | 113.73 |
| 20 | 112.8 |
| 21 | 115.34 |
| 22 | 121.87 |
| 23 | 121.87 |
| 24 | 111.03 |
| 25 | 162.53 |

The eluate fractions were light yellow and clear.

The eluates were neutralized to pH 5 with 2 M tris base and after that they were 0.2 μm filtrated. Actual volume of 2 M Tris base was included in the weight of the eluates above. Titer was determined in all fractions by the MagSelect SuRe HiTrap bind and elute assay, see above.

Finally Fractions 7-18 were pooled and 1 mL of this pool were diluted 20× with 200 mM Na-Phosphate pH 6.8 in a 1.5 mL HPLC vial and analysed with analytical size exclusion chromatography (SEC) on the HPLC system and compared with the mAb standard (that was diluted 8× with same buffer).

The Mag Sepharose in the separator was released and pumped back into a vessel. The resin was washed with 2 cv 1 M NaOH for 30 minutes on a G3 glass filter, it was equilibrated with 5 cv PBS and finally it was washed with 2 cv 20% Ethanol as preservation solution and the resin was transferred back into a plastic bottle with 20% EtOH for storage.

Purity by SEC Method

Injection volume: 10 μL

Flow: 0.8 mL/min

Column: Superdex 200 Increase 10/300 GL

Stop time: 26 min

Detection at 214 nm.

HCP Analysis

In the Start and pool eluate samples, 504 preservation solution was added to 450 μL sample prior to the host cell protein (HCP) analysis.

Analysis was performed using a 3rd generation CHO-HCP ELISA kit (Cygnus) on a Gyrolab workstation (Gyros Protein Technologies) with software package 5.3.0.

Results, Analysis and Conclusions

Figure 5A:
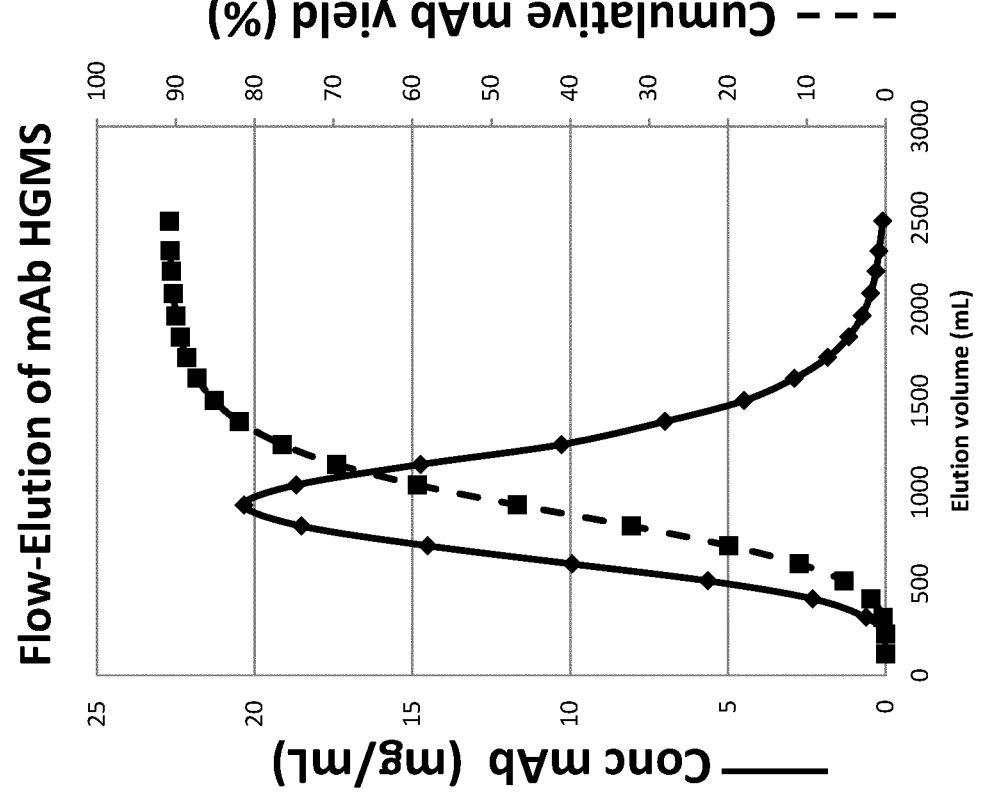
FIGS. 5A, 5B, and 5C are graphs showing the elution curves from a monoclonal antibody (mAb) experiment described in Example 2 below.

FIG. 5A shows the elution profile of the mAb from the magnetic separator. The pooled fraction, fractions 7-18, corresponding to 1.2 L eluate shows that 87% mAb yield can be obtained with 3 bed volumes (one bed volume=400 mL) elution buffer. The concentration in the pooled eluate was 10.7 mg/mL which is a 4× concentration. The binding yield in the incubation step was 94% and the total elution yield was 91%.

Figure 5B:
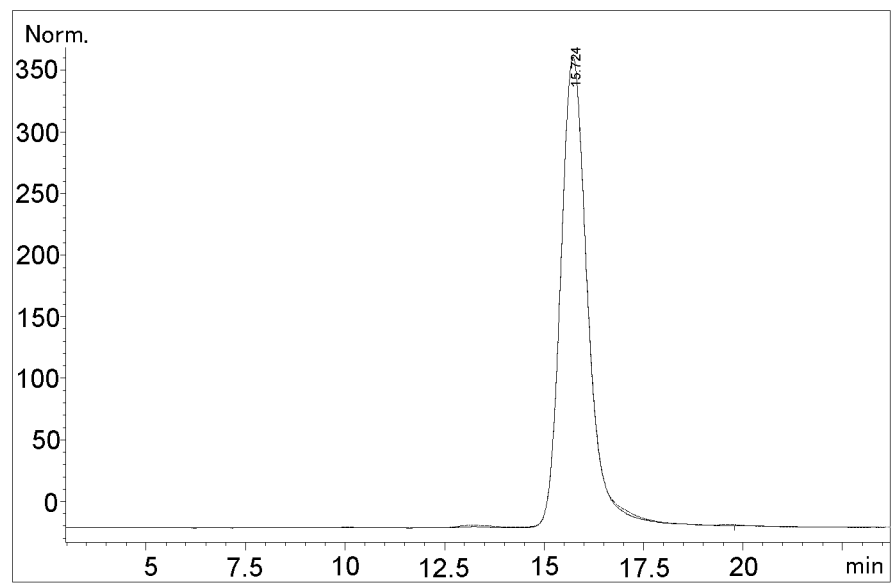
Figure 5C:
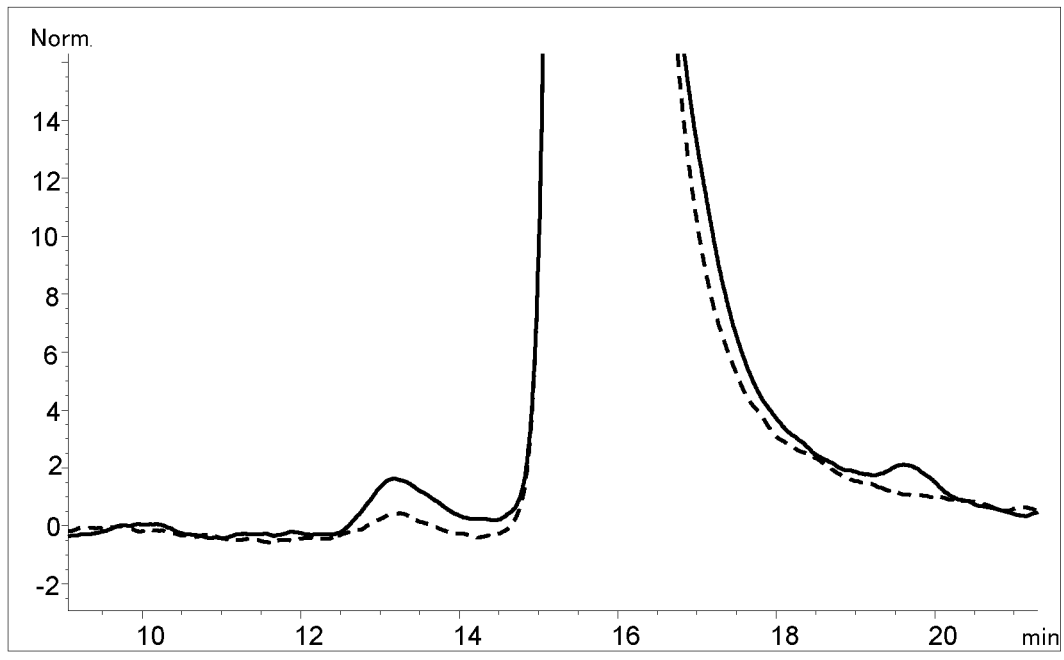

The pooled sample was analysed by SEC and HCP assay and compared with a pure mAb standard. The results are shown in FIG. 5B (smaller scale) and FIG. 5C (larger scale; zooming in on the base of the peaks). The solid line is the pooled mAb eluate and the dotted line is the pure mAb standard. The chromatogram is normalized. The aggregate peak, main peak and peak after main peak was integrated and the purity was determined to 98.5%.

Example 3

Purpose

The purpose of this study was to investigate which mixing speed (rotor speed) and flow can be used for the flow-elution of IgG from Mag Sepharose PrismA, using magnetic fluidized beads without migration of beads. It was also investigated how the IgG elution profile was affected by different mixing speed, volume of beads and bead sizes.

Equipment

HGMS Separator, MES100RS serial no 400213239, Andritz Gmbh

Mixer at incubation, IL82274-3, Janke-Kunkel

UV reader, Spectra Max™ plus, Molecular Devices

UV reading plate, 96 well, 3635 lot 33918007, Corning

Balance, PG 5002 Delta Range, Mettler

Plastic bottles 130 mL

25 L plastic buffer bottles

Mag Sepharose prismA 0-37 µm Lot LS-033447, GE Healthcare

Mag Sepharose PrismA 37-100 µm LS-32871, GE Healthcare

Materials

Human IgG, Gammanorm 165 mg/mL, Octapharma $NaH_2PO_4 \cdot H_2O$, pa, Merck $Na_2HPO_4 \cdot 2\ H_2O$ pa, Merck NaCl, pa, Merck Acetic acid, pa, Merck Na-acetate·3 $H_2O$, pa, Merck Conditions and Observations Preparation of Solutions:

A-Buffer, 20 mM $PO_4$+0.15 M NaCl pH 7.5

| Buffer salt amount (g) | Component | Mw (g/mol) |
|---|---|---|
| 11.356 | NaH2PO4 (×1 H2O) | 137.99 |
| 74.347 | Na2HPO4 (×2 H2O) | 177.99 |
| 219.15 | NaCl | 58.44 |
| 25 liter | Final volume with water | |

B-Buffer, 0.1 M Na-Acetate pH 3.2

| Buffer salt amount (g) | Component | Mw (g/mol) |
|---|---|---|
| 139.853 ml | Acetic acid | 60.05 |
| 7.431 | Na-acetate (×3 H2O) | 136.08 |
| 25 liter | Final volume with water | |

IgG 2 mg/mL 73 mL of IgG (Gammanorm) was diluted to 6 L A-buffer to obtain an IgG concentration of ~2.0 mg/mL.

Test of Rotor Speed and Flow to Investigate Bead Losses 100 mL, 300 mL or 400 mL (wet sedimented resin) Mag Sepharose Prisma 37-100 µm or 0-37 µm was pumped into the HGMS system with the magnet turned on. The rotor was turned on at different speeds and the flow pump with A-buffer was also varied to investigate at which rotor speed and flow rate the magnetic beads start to migrate (visually) from the HGMS chamber.

The results are shown in tables 6-10 below.

Loading 100 mL Mag Sepharose 0-37 µm: Beads were trapped up to 2100 mL/min with a rotor speed of 150 rpm. Beads start to migrate out of the HGMS at 225 rpm rotor speed.

Loading 300 mL Mag Sepharose 0-37 µm: Beads were trapped up to 560 mL/min with a rotor speed of 75 rpm.

Loading 100 mL Mag Sepharose 37-100 µm: Beads were trapped up to 2100 mL/min with a rotor speed of 150 rpm.

Loading 300 mL Mag Sepharose 37-100 µm: Beads were trapped up to 560 mL/min with a rotor speed of 150 rpm. The beads are also still trapped at 300 rpm rotor speed at 140 mL/min.

Loading 400 mL Mag Sepharose 37-100 µm: Beads were trapped up to 1400 mL/min with a rotor speed of 75 rpm.

It was possible to run higher flow rate for all loadings at lower rotor speed than the rotor speed where beads start to migrate out from the HGMS system, see tables.

TABLE 6

Magnetic bead migration study on 100 mL Mag Sepharose 0-37 µm 100 mL Mag Sepharose 0-37 µm

| Flow rate settings (%) | Flow rate (mL/min) | 0%, 0 rpm | 5%, 75 rpm | 10%, 150 rpm | 15% 225 rpm | 20%, 300 rpm |
|---|---|---|---|---|---|---|
| 5 | 140 | Not tested | Not tested | X | ○ | ○ |
| 10 | 280 | Not tested | Not tested | X | Not tested | ○ |
| 20 | 560 | Not tested | Not tested | X | Not tested | Not tested |
| 30 | 840 | Not tested | Not tested | Not tested | Not tested | Not tested |
| 40 | 1120 | Not tested | Not tested | Not tested | Not tested | Not tested |
| 50 | 1400 | X | Not tested | X | Not tested | Not tested |
| 60 | 1680 | Not tested | Not tested | Not tested | Not tested | Not tested |
| 70 | 1960 | Not tested | Not tested | Not tested | Not tested | Not tested |
| 75 | 2100 | X | Not tested | X | Not tested | Not tested |
| 80 | 2240 | Not tested | Not tested | Not tested | Not tested | Not tested |
| 100 | 2800 | Not tested | Not tested | Not tested | Not tested | Not tested |

X = No particle leakage,

○ = particle migrates from separation chamber

TABLE 7

Magnetic bead migration study on 300 mL Mag Sepharose 0-37 μm.
300 mL Mag Sepharose 0-37 μm Flow rates

| Flow rate settings | Flow rate | Rotor speed (%, rpm) | | | | |
|---|---|---|---|---|---|---|
| (%) | (mL/min) | 0%, 0 rpm | 5%, 75 rpm | 10%, 150 rpm | 15% 225 rpm | 20%, 300 rpm |
| 5 | 140 | Not tested | X | ○ | Not tested | Not tested |
| 10 | 280 | Not tested | X | ○ | Not tested | Not tested |
| 20 | 560 | Not tested | X | Not tested | Not tested | Not tested |
| 30 | 840 | Not tested | ○ | Not tested | Not tested | Not tested |
| 40 | 1120 | Not tested | Not tested | Not tested | Not tested | Not tested |
| 50 | 1400 | X | ○ | Not tested | Not tested | Not tested |
| 60 | 1680 | Not tested | Not tested | Not tested | Not tested | Not tested |
| 70 | 1960 | Not tested | Not tested | Not tested | Not tested | Not tested |
| 75 | 2100 | X | Not tested | Not tested | Not tested | Not tested |
| 80 | 2240 | Not tested | Not tested | Not tested | Not tested | Not tested |
| 100 | 2800 | Not tested | Not tested | Not tested | Not tested | Not tested |

X = No particle leakage,
○ = particle migrates from separation chamber

TABLE 8

Magnetic bead migration study on 100 mL Mag Sepharose 37-100 μm.
100 mL Mag Sepharose 37-100 μm Flow rates

| Flow rate settings | Flow rate | Rotor speed (%, rpm) | | | | |
|---|---|---|---|---|---|---|
| (%) | (mL/min) | 0%, 0 rpm | 5%, 75 rpm | 10%, 150 rpm | 15% 225 rpm | 20%, 300 rpm |
| 5 | 140 | Not tested | X | X | Not tested | ○ |
| 10 | 280 | X | Not tested | X | Not tested | ○ |
| 20 | 560 | Not tested | X | X | Not tested | ○ |
| 30 | 840 | Not tested | Not tested | Not tested | Not tested | Not tested |
| 40 | 1120 | Not tested | Not tested | Not tested | Not tested | Not tested |
| 50 | 1400 | X | Not tested | X | Not tested | Not tested |
| 60 | 1680 | Not tested | Not tested | Not tested | Not tested | Not tested |
| 70 | 1960 | Not tested | Not tested | Not tested | Not tested | Not tested |
| 75 | 2100 | X | Not tested | X | Not tested | Not tested |
| 80 | 2240 | Not tested | Not tested | Not tested | Not tested | Not tested |
| 100 | 2800 | Not tested | Not tested | Not tested | Not tested | Not tested |

X = No particle leakage,
○ = particle migrates from separation chamber

TABLE 9

Magnetic bead migration study on 300 mL Mag Sepharose 37-100 μm.
300 mL Mag Sepharose 37-100 μm Flow rates

| Flow rate settings | Flow rate | Rotor speed (%, rpm) | | | | |
|---|---|---|---|---|---|---|
| (%) | (mL/min) | 0%, 0 rpm | 5%, 75 rpm | 10%, 150 rpm | 15% 225 rpm | 20%, 300 rpm |
| 5 | 140 | Not tested | Not tested | X | Not tested | X |
| 10 | 280 | Not tested | Not tested | X | Not tested | ○ |
| 20 | 560 | X | Not tested | X | Not tested | ○ |
| 30 | 840 | X | Not tested | Not tested | Not tested | Not tested |
| 40 | 1120 | Not tested | Not tested | Not tested | Not tested | Not tested |
| 50 | 1400 | X | Not tested | ○ | Not tested | Not tested |
| 60 | 1580 | X | Not tested | Not tested | Not tested | Not tested |
| 70 | 1960 | Not tested | Not tested | Not tested | Not tested | Not tested |
| 75 | 2100 | Not tested | Not tested | ○ | Not tested | Not tested |

TABLE 9-continued

Magnetic bead migration study on 300 mL Mag Sepharose 37-100 μm.

300 mL Mag Sepharose 37-100 μm

| | | Flow rates | | | | |
|---|---|---|---|---|---|---|

| Flow rate settings | Flow rate | | | Rotor speed (%, rpm) | | |
|---|---|---|---|---|---|---|
| (%) | (mL/min) | 0%, 0 rpm | 5%, 75 rpm | 10%, 150 rpm | 15% 225 rpm | 20%, 300 rpm |
| 80 | 2240 | X | Not tested | Not tested | Not tested | Not tested |
| 100 | 2800 | Not tested | Not tested | Not tested | Not tested | Not tested |

X = No particle leakage,
○ = particle migrates from separation chamber

15

TABLE 10

Magnetic bead migration study on 400 mL Mag Sepharose 37-100 μm.

400 mL Mag Sepharose 37-100 μm

| | | Flow rates | | | | |
|---|---|---|---|---|---|---|

| Flow rate settings | Flow rate | | | Rotor speed (%, rpm) | | |
|---|---|---|---|---|---|---|
| (%) | (mL/min) | 0%, 0 rpm | 5%, 75 rpm | 10%, 150 rpm | 15% 225 rpm | 20%, 300 rpm |
| 5 | 140 | Not tested | X | ○ | ○ | ○ |
| 10 | 280 | X | X | ○ | Not tested | Not tested |
| 20 | 560 | X | X | Not tested | Not tested | Not tested |
| 30 | 840 | X | X | Not tested | Not tested | Not tested |
| 40 | 1120 | Not tested | Not tested | Not tested | Not tested | Not tested |
| 50 | 1400 | X | X | Not tested | Not tested | Not tested |
| 60 | 1680 | Not tested | Not tested | Not tested | Not tested | Not tested |
| 70 | 1960 | Not tested | Not tested | Not tested | Not tested | Not tested |
| 75 | 2100 | X | Not tested | Not tested | Not tested | Not tested |
| 80 | 2240 | Not tested | Not tested | Not tested | Not tested | Not tested |
| 100 | 2800 | Not tested | Not tested | Not tested | Not tested | Not tested |

X = No particle leakage,
○ = particle migrates from separation chamber

Flow Elution of IgG Study 400 mL of each resin prototype was incubated for >1 h with 6 L of the IgG 2 mg/mL sample.

100 or 400 mL (1.6 L or 6.4 L of IgG resin mixture) of the IgG adsorbed Mag Sepharose PrismA was pumped into the system and the magnetic beads were trapped by the magnet and the beads were washed three times with 1 L A-buffer.

Elution was performed at different rotor speed at 140 mL/min to investigate how bead volume and rotor speed affect elution performance.

At elution, ~100-2100 mL fractions were collected and the absorbance was determined for each fraction using a UV plate reader, and also the exact volume in each fraction was determined using weighing. The UV for each fraction was plotted against the cumulative elution volume. See FIGS. 1-4.

In general, 0% rotor rotation showed insufficient elution of the IgG since after several column volumes of elution buffer, >4000 mL, high concentration of IgG was still present in the eluate and the elution profile showed no tendency to decline in concentration.

Figure 8A:
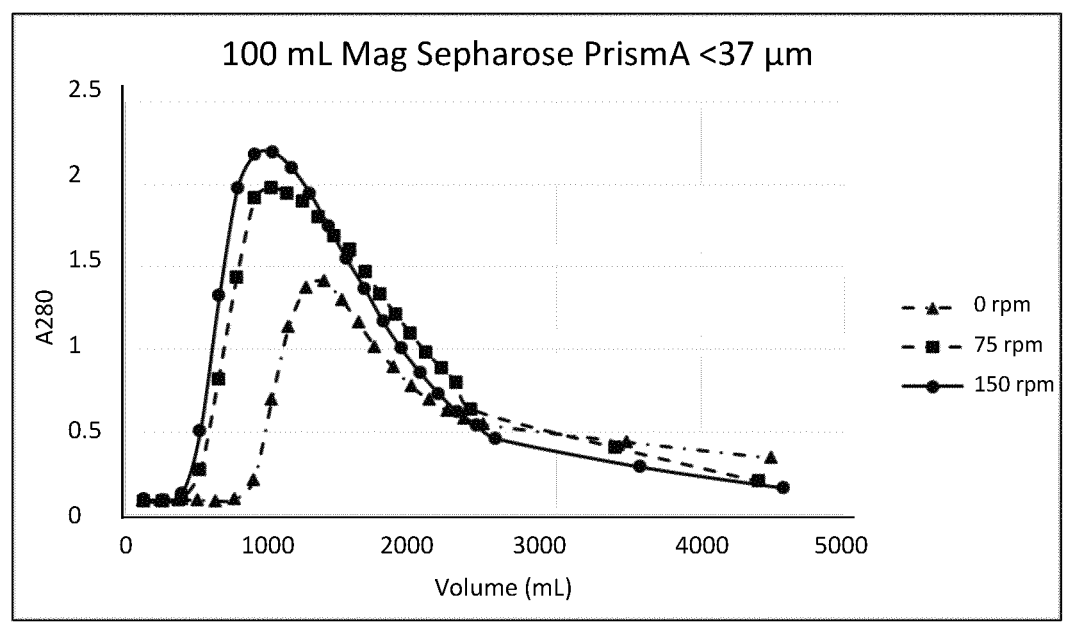
FIGS. 8A, 8B, 8C, and 8D are graphs showing the elution curves from a monoclonal antibody (mAb) experiment described in Example 3 below.
Figure 8B:
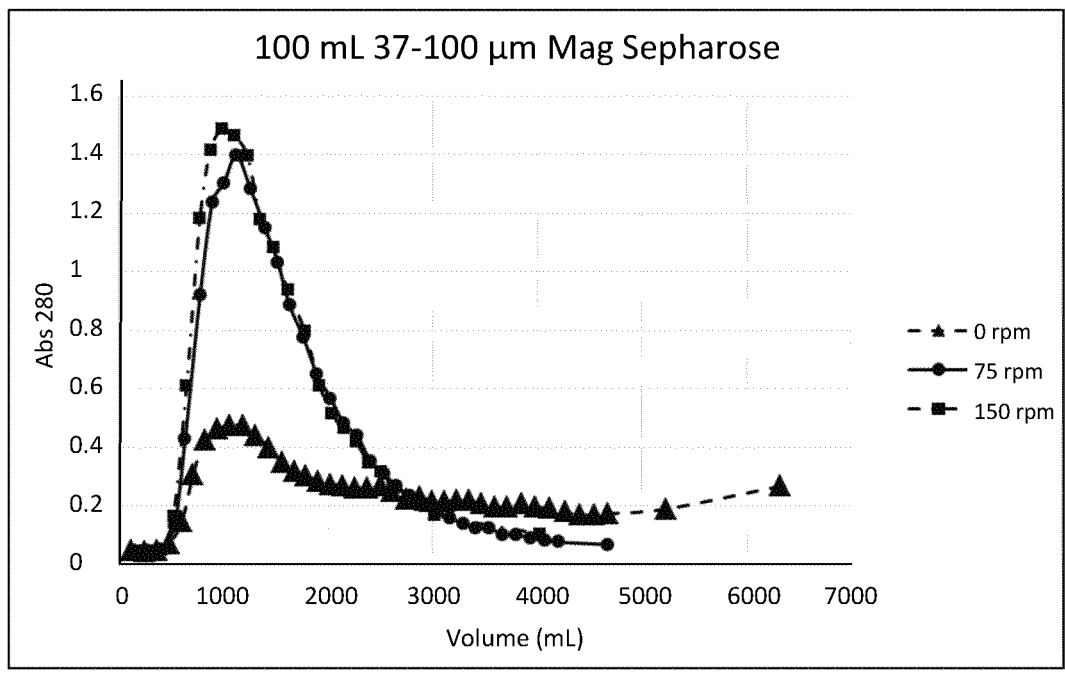
Figure 8C:
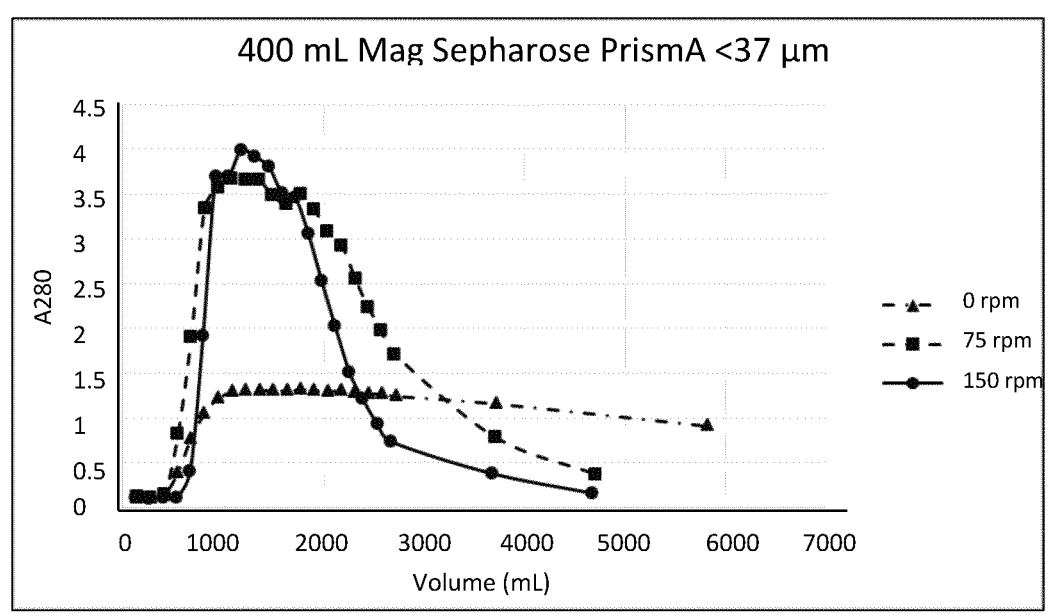

For the <37 μm beads, less volume of beads leads to less dependence of rotor speed. The shape of the elution peak for 75 and 150 rpm rotor speed for 100 mL beads were similar (FIG. 8A). For 400 mL beads the shape of the elution peaks differed more significantly between rotor speeds, with the most effective elution of IgG using 150 rpm (FIG. 8C).

Figure 8D:
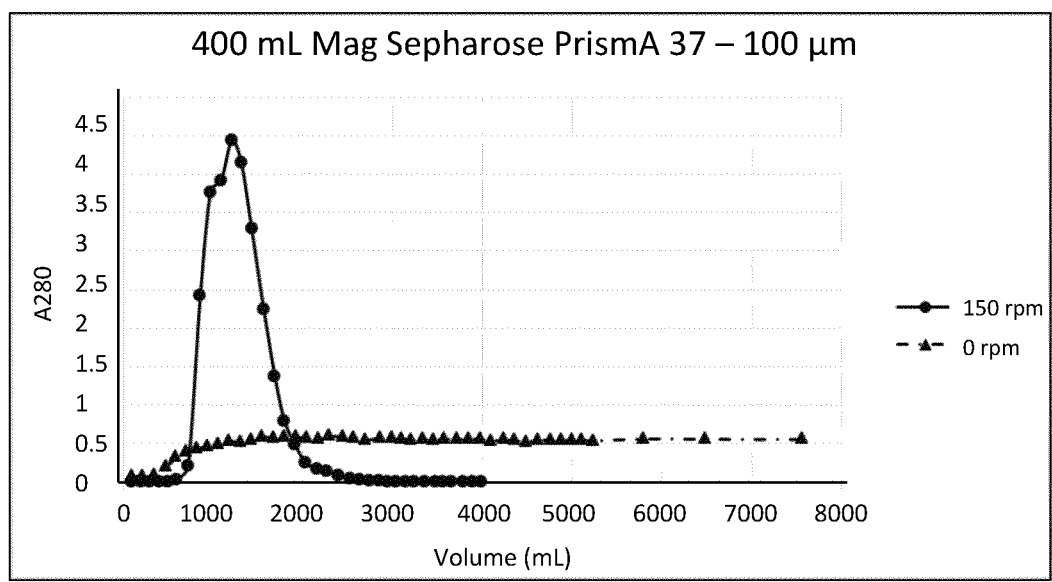

For the 37-100 μm beads, less volume of beads leads to less dependence of rotor speed. For 100 mL beads, the elution peak for 75 rpm rotor speed and 150 rpm rotor speed were similar (FIG. 8B). For 400 mL beads the shape of the elution peak differed dramatically between 150 rpm rotation and 0 rpm rotation. At 150 rpm rotation the IgG was eluted off in a symmetric elution peak while at 0 rpm rotation the IgG was still eluting off after 6500 mL elution buffer (FIG. 8D).

Comparing 0-37 μm beads with 37-100 μm beads, the elution peak shapes are similar using 100 mL beads (see FIG. 8A and FIG. 8B, respectively). At 400 mL beads and 150 rpm rotation, the larger beads, 37-100 μm, showed much sharper elution peak than the elution peak for 400 mL<37 μm beads. Using the larger beads, a majority of IgG seems to be eluted off before 2000 mL elution buffer while for the <37 μm beads the elution peak has not reached down to a stable baseline at 4000 mL (see FIG. 8C and FIG. 8D, respectively).

Example 4

Purpose

The purpose of this study was to evaluate the effect of adding a membrane chromatography step for polishing of a biomolecule after magnetic separation. More particularly, the study comprised polishing of an IgG1 monoclonal antibody (mAb) by membrane chromatography with Fibro adhere unit prototypes after purification with Mag Sepharose PrismA by use of a High Gradient Magnetic Separator system.

Materials

Start sample: IgG1 monoclonal antibody from an XDR-10 cultivation in CHO cells, viability 66.4%, concentration of 2.7 g/L Superdex™ 200 Increase 10/300 GL, GE Healthcare MagSepharose PrismA 37-100 μm, 400 ml, GE Health-care Fibro Adhere unit prototypes, 0.4 ml:

Fibro Adhere 1: The material was crosslinked with divinylsulfone (DVS) after the addition of allyl glycidyl ether (AGE), with an Adhere reaction concentration of 167 g/Ltr. Titration of 563 umol/g.

Fibro Adhere 2: The material was crosslinked with DVS before the AGE was added, with an Adhere reaction concentration of 167 g/Ltr. Titration of 212 umol/g.

Fibro Adhere 3: The material was crosslinked with DVS before the AGE was added with an Adhere reaction concentration of 500 g/Ltr. Titration of 478 umol/g.

Equipment

ÄKTA™ Pure 25, GE Healthcare

HPLC Infinity 1200, Agilent technologies

Buffers 25 mM Na-Phosphate+0.15 M NaCl pH 6.3

4.88 g Na $NaH_2PO_4 \cdot H_2O$, 2.6 g $Na_2HPO_4$ and 17.5 g NaCl was diluted and mixed with 2 L $dH_2O$ 25 mM Na-Phosphate pH 7

1.16 g Na $NaH_2PO_4 \cdot H_2O$, and 2.367 g $Na_2HPO_4$ was diluted and mixed with 1 L $dH_2O$ 25 mM Na-Phosphate+1M NaCl pH 7

11. The equilibration was performed at a flowrate of 16 ml/min for 50 unit volumes (20 ml) before 4 ml of the mAb sample was applied at 16 ml/min and the flowthrough collected. The Fibro Adhere unit was washed with 20 unit volumes (8 ml) and cleaned with 100 mM Acetic acid pH 3.0 for 25 unit volumes (10 ml) at a flowrate of 16 ml/min before re-equilibration for 50 unit volumes (20 ml). The UV was monitored at all times at 280 nm.

TABLE 11

Buffer conditions of mAb polishing with Fibro Adhere.

| Buffer | pH | Conductivity |
|---|---|---|
| 1 | 6.3 | 18 mS/cm |
| 2 | 7.0 | 10 mS/cm |
| 3 | 7.5 | 3.5 mS/cm |

Results, Analysis and Conclusions

The chromatograms from mAb polishing with Fibro Adhere at the varying buffer conditions showed a high UV value during the sample application at all three buffer conditions. The flowthrough of sample during sample application was collected and further analyzed, see table 12. The concentration of mAb and percentage of aggregates were analysed by SEC-HPLC, Superdex 200 increase 10/300 GL at a flowrate of 0.8 ml/min for 26 min per sample with 0.2 M Na phosphate buffer. The host cell protein level in the flow-through fractions were analysed with Cygnus 3rd generation CHO HCP ELISA kit.

TABLE 12

Results from evaluation of mAb polishing with Fibro Adhere prototypes in flowthough mode at different buffer conditions. The start material was mAb purified from MagSepharose PrismA with a titer of ~3 mg/ml and HCP of 160 ppm.

| | Buffer conditions | | | | | |
|---|---|---|---|---|---|---|
| | pH 6.6 18 mS/cm | | pH 7.0 10 mS/cm | | pH 7.5 3.5 mS/cm | |
| Prototypes | Yield (%) | HCP ppm | Yield (%) | HCP ppm | Yield (%) | HCP ppm |
| Fibro Adhere 1 | 97 | 111 | 99 | 54 | 99 | 26 |
| Fibro Adhere 2 | 104 | 135 | 102 | 79 | 98 | 32 |
| Fibro Adhere 3 | 90 | 172 | 102 | 57 | 93 | 25 |

0.464 g Na $NaH_2PO_4 \cdot H_2O$, 3.851 g $Na_2HPO_4$ and 58.44 g NaCl was diluted and mixed with 1 L $dH_2O$ 25 mM Na-Phosphate pH 7.5

0.73 g Na $NaH_2PO_4 \cdot H_2O$, and 3.508 g $Na_2HPO_4$ was diluted and mixed with 1 L $dH_2O$ 100 mM Acetic acid pH 3.0

6 ml Glacial Acetic acid was diluted and mixed with 1 L $dH_2O$

Conditions and Observations

The eluate from MagSepharose PrismA using the High Gradient Magnetic Separator system, as described in Example 2, was used for further polishing by membrane chromatography with Fibro adhere unit prototypes.

Fibro Adhere units were connected to an ÄKTA Pure 25 system and three different 25 mM Na-phosphate buffer conditions (pH and conductivity) were evaluated, see table In conclusion, the polishing of mAb resulted in high yields, 93-100%, and in a substantial reduction of host cell proteins (HCP). The highest HCP reduction was with pH 7.5 and at a conductivity of 3.5 mS/cm, which resulted in a 93-99% yield, and the HCP reduction was highest with the Fibro Adhere prototypes with the highest ligand densities.

It is to be understood that the present disclosure is not restricted to the above-described exemplifying embodiments thereof and that several conceivable modifications of the present disclosure are possible within the scope of the following claims.

The invention claimed is:

1. A method for separating a biomolecule from a cell culture, comprising the steps of:

(a) providing magnetic particles comprising ligands capable of binding the biomolecule;

(b) contacting a cell culture comprising the biomolecule with the magnetic particles to obtain magnetic particles comprising the bound biomolecule;

(c) retaining the magnetic particles with a magnetic field in a magnetic separator;

(d) washing the magnetic particles at least once with a washing liquid in continuous mode, wherein the wash comprises the following substeps:

(d1) agitating the magnetic particles in at least one plane of the magnetic separator by applying an oscillating magnetic field to form a fluidised bed of magnetic particles in the magnetic separator, and (d2) providing a flow of a washing liquid in a direction essentially perpendicular to the at least one plane to remove the cell culture while retaining the magnetic particles in the magnetic field, wherein the flow of washing liquid comprises simultaneous introduction and removal of washing liquid;

(e) agitating the magnetic particles in at least one plane of the magnetic separator by applying an oscillating magnetic field to form a fluidised bed of magnetic particles in the magnetic separator; and (f) providing a flow of an elution liquid in a direction essentially perpendicular to the at least one plane, to elute the bound biomolecule from the magnetic particles while retaining the magnetic particles with the magnetic field in the magnetic separator, wherein steps (c) and (d) are performed simultaneously.

2. The method according to claim 1, wherein step (b) or (c) comprises adding the magnetic particles to a magnetic separator comprising at least one agitator, and step (e) comprises agitating the magnetic particles by switching on the agitator(s).

3. The method according to claim 1, wherein step (e) comprises agitating the magnetic particles in a plurality of essentially parallel planes of the magnetic separator to form a plurality of fluidized beds of magnetic particles, and wherein step (f) comprises providing the flow of the elution liquid in a direction essentially perpendicular to the plurality of planes.

4. The method according to claim 1, wherein the biomolecule is eluted with a maximum of 10 bed volumes of elution liquid.

5. The method according to claim 1, wherein at least steps (c)-(f), are performed in the magnetic separator.

6. The method according to claim 1, wherein step (b) comprises:

(i) adding the magnetic particles to a magnetic separator, followed by providing a feed from the cell culture to the magnetic separator, or (ii) providing a feed from a mixture of the cell culture and the magnetic particles comprising the bound biomolecule to a magnetic separator.

7. The method according to claim 1, wherein steps (b)-(f) are carried out in a combined bioreactor vessel/contactor and magnetic separator.

8. The method according to claim 1, wherein step (d) is performed and repeated at least once before proceeding to step (e).

9. The method according to claim 1, wherein the elution liquid in step (f) has a linear flow rate in a range of from 10 to 3000 cm/h.

10. The method according to claim 2, wherein the agitator (s) in step (e) rotate(s) at a speed in a range of from 15 to 1500 rpm.

11. The method according to claim 1, wherein the magnetic separator is connected to a chromatography system.

12. The method according to claim 1, wherein the magnetic particles have a volume-weighted median diameter (d50, v) in a range of from 8 to 300 μm.

13. The method according to claim 1, wherein the magnetic particles have an average density of 1.05-1.20 g/ml sedimented particles.

14. The method according to claim 1, wherein each of the magnetic particles comprises a porous polymer matrix and one or more magnetic granules embedded in the porous polymer matrix.

15. The method according to claim 14, wherein each of the magnetic particles comprises 5-15 wt. % of the magnetic granules.

16. The method according to claim 14, wherein the magnetic granules have a volume-weighted median diameter (d50, v) of from 1 to 5 μm.

17. The method according to claim 14, wherein each of the magnetic particles comprises a concentration of magnetic granules in a central region of the particle of at least 200% of the concentration in a surface region of the particle, wherein the central region is defined as having a distance of >0.2 particle radii from the particle surface and the surface region is defined as having a distance of <0.2 particle radii from the particle surface.

18. The method according to claim 4, wherein the biomolecule is eluted with a maximum of 4 bed volumes.

19. The method according to claim 4, wherein the biomolecule is eluted with a maximum of 3 bed volumes.

20. The method according to claim 5, wherein the magnetic separator is a high gradient magnetic separation system.

21. The method according to claim 9, wherein the linear flow rate of the elution liquid in step (f) is in a range of from 50 to 600 cm/h.

22. The method according to claim 10, wherein the speed of the agitator(s) in step (e) is in a range of from 50 to 300 rpm.

23. The method according to claim 12, wherein the magnetic particles have a volume-weighted median diameter (d50, v) in a range of from 37 to 100 μm.

\* \* \* \* \*